US008673843B2

(12) United States Patent
Moskal et al.

(10) Patent No.: US 8,673,843 B2
(45) Date of Patent: *Mar. 18, 2014

(54) NMDA RECEPTORS MODULATORS AND USES THEREOF

(75) Inventors: Joseph Moskal, Evanston, IL (US); M. Amin Khan, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,861

(22) Filed: Jun. 18, 2012

(65) Prior Publication Data

US 2013/0035292 A1   Feb. 7, 2013

Related U.S. Application Data

(63) Continuation-in-part of application No. PCT/US2011/024583, filed on Feb. 11, 2011.

(60) Provisional application No. 61/550,782, filed on Oct. 24, 2011, provisional application No. 61/303,472, filed on Feb. 11, 2010.

(51) Int. Cl.
   *A61K 38/00* (2006.01)

(52) U.S. Cl.
   USPC ............................................. 514/1.1

(58) Field of Classification Search
   None
   See application file for complete search history.

(56) References Cited

U.S. PATENT DOCUMENTS

| | | | |
|---|---|---|---|
| 4,904,681 A | 2/1990 | Cordi et al. |
| 4,959,493 A | 9/1990 | Ohfune et al. |
| 5,061,721 A | 10/1991 | Cordi et al. |
| 5,086,072 A | 2/1992 | Trullas et al. |
| 5,166,136 A | 11/1992 | Ward et al. |
| 5,350,769 A | 9/1994 | Kasai et al. |
| 5,523,323 A | 6/1996 | Maccecchini |
| 5,605,911 A | 2/1997 | Olney et al. |
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,521,414 B2 | 2/2003 | Melcher et al. |
| 6,541,453 B2 | 4/2003 | Oldham et al. |
| 6,635,270 B2 | 10/2003 | Hong et al. |
| 6,667,317 B2 | 12/2003 | Chenard et al. |
| 6,821,985 B2 | 11/2004 | Chenard et al. |
| 7,273,889 B2 | 9/2007 | Mermelstein et al. |
| 7,884,080 B2 | 2/2011 | Aslanian et al. |
| 8,492,340 B2 | 7/2013 | Moskal et al. |
| 2003/0022253 A1 | 1/2003 | Moskal |
| 2003/0064921 A1 | 4/2003 | Millhauser et al. |
| 2003/0175734 A1 | 9/2003 | Kroes et al. |
| 2005/0037433 A1 | 2/2005 | Nakanishi et al. |
| 2005/0118286 A1 | 6/2005 | Suffin et al. |
| 2006/0241046 A1 | 10/2006 | Olivera et al. |
| 2007/0087404 A1 | 4/2007 | Stahl et al. |
| 2007/0208001 A1 | 9/2007 | Zhuo et al. |
| 2011/0306586 A1 | 12/2011 | Khan et al. |
| 2012/0178695 A1 | 7/2012 | Moskal |
| 2012/0295852 A1 | 11/2012 | Moskal |
| 2013/0005662 A1 | 1/2013 | Moskal |
| 2013/0035292 A1 | 2/2013 | Moskal et al. |
| 2013/0053325 A1 | 2/2013 | Moskal et al. |
| 2013/0136954 A1 | 5/2013 | Fujita et al. |
| 2013/0288975 A1 | 10/2013 | Moskal et al. |
| 2013/0296248 A1 | 11/2013 | Moskal et al. |
| 2013/0310323 A1 | 11/2013 | Moskal et al. |

FOREIGN PATENT DOCUMENTS

| | | |
|---|---|---|
| CN | 101066945 A | 11/2007 |
| CN | 101125817 A | 2/2008 |
| WO | WO-97/43306 A1 | 11/1997 |
| WO | WO 9902733 A1 * | 1/1999 |
| WO | WO-99/24584 A1 | 5/1999 |
| WO | WO-99/51985 A1 | 10/1999 |
| WO | WO-00/28090 A2 | 5/2000 |
| WO | WO-01/36685 A2 | 5/2001 |
| WO | WO-01/96606 A2 | 12/2001 |
| WO | WO-01/98367 A2 | 12/2001 |
| WO | WO-02/47535 A2 | 6/2002 |
| WO | WO-02/072609 A2 | 9/2002 |

(Continued)

OTHER PUBLICATIONS

Abbott et al. (1995) "The Formalin Test: Scoring Properties of the First and Second Phases of the Pain Response in Rats," Pain, vol. 60, Issue 1, pp. 91-102.
Bennett et al. (1988) "A Peripheral Mononeuropathy in Rat That Produces Disorders of Pain Sensation Like Those Seen in Man," Pain, vol. 33, Issue 1, pp. 87-107.
Burch et al. (2010) "GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder," *NCDEU*, Jun. 16, 2010, Naurex, Inc. (1 page).
Burgdorf et al. (2008) "Uncovering the Molecular Basis of Positive Affect Using Rough-and-Tumble Play in Rats: A Role for the NMDA Receptor and Implications for Depression," (2 pages) (Poster #393. 1/UU11) *Neuroscience 2008*, Nov. 17, 2008.

(Continued)

*Primary Examiner* — Marcela M Cordero Garcia
*Assistant Examiner* — Kaipeen Yang
(74) *Attorney, Agent, or Firm* — Goodwin Procter LLP

(57) ABSTRACT

Disclosed are compounds having enhanced potency in the modulation of NMDA receptor activity. Such compounds are contemplated for use in the treatment of diseases and disorders, such as learning, cognitive activities, and analgesia, particularly in alleviating and/or reducing neuropathic pain. Orally available formulations and other pharmaceutically acceptable delivery forms of the compounds, including intravenous formulations, are also disclosed.

12 Claims, No Drawings

(56) References Cited

FOREIGN PATENT DOCUMENTS

| | | | |
|---|---|---|---|
| WO | WO-03/010540 A1 | 2/2003 | |
| WO | WO-2005/020973 A2 | 3/2005 | |
| WO | WO-2007027559 A2 | 3/2007 | |
| WO | WO 2007027559 A2 * | 3/2007 | |
| WO | WO-2009/039390 A2 | 3/2009 | |
| WO | WO-2010/015545 A1 | 2/2010 | |
| WO | WO-2010/033757 A1 | 3/2010 | |
| WO | WO-2010/065709 A2 | 6/2010 | |
| WO | WO-2011/003064 A2 | 1/2011 | |
| WO | WO-2011/044089 A2 | 4/2011 | |
| WO | WO-2011/100585 A1 | 8/2011 | |
| WO | WO-2012/149389 A1 | 11/2012 | |

OTHER PUBLICATIONS

Burgdorf et al. (2010) "The Antidepressant and Anxiolytic Properties of GLYX-13: A Novel NMDA Receptor Glycine Site Functional Partial Agonist," (Poster #198) *ACNP 2010*, Dec. 6, 2010 (1 page).
Burgdorf et al. (2011) "The N-Methyl-D-Aspartate Receptor Modulator GLYX-13 Enhances Learning and Memory, in Young Adult and Learning Impaired Aging Rats," *Neurobiol. Aging*, 32(4):698-706.
Forni (1998) "Two Diastereoisomers of 2-(Benzenesulfonyl)-5-benzoyl-1-oxo-3-phenyl-2,5-diazaspiro[3.4]octan-7-yl acetate," Acta Crystallographica Section C: Crystal Structure Communications, C54(9):1320-1322.
Foster et al. "Neurobiology: Taking Apart NMDA Receptors," *Nature* vol. 329, Oct. 1987, pp. 395-396.
Golik (1972) "Synthesis of Malonimide Derivatives as Potential Penicillin Analogs," J. Heterocycl. Chem., 9(1):21-4.
Grigg et al. (1995) "X=Y-ZH Systems as Potential 1,3-Dipoles. Part 46. Cascade 1,3-Dipolar Cycloaddition Reactions of Cephalosporin Imines," *Tetrahedron*, 51(48):13347-56.
Haring et al. "Binding Studies and Photoaffinity Labeling Identify Two Classes of Phencyclidine Receptors in Rat Brain," Biochemistry, vol. 26, 1987, pp. 5854-5861.
Haring et al. (1986) "Identification of Polypeptides of the Phencyclidine Receptor of Rat Hippocampus by Photoaffinity Labeling with [H3]Azidophencyclidine," *Biochemistry* vol. 25, pp. 612-620.
Haring et al. (1987) "Multiple Mode of Binding of Phencyclidines: High Affinity Association Between Phencyclidine Receptors in Rat Brain and a Monovalent Ion-Sensitive Polypeptide," *Biochem. Biophys. Res. Comm.*, vol. 142, No. 2, pp. 501-510.
Haring et al. (1991) "Glycine-Like Modulation of N-Methyl-D-Aspartate Receptors by a Monoclonal Antibody that Enhances Long-Term Potentiation," *J. Neurochem.*, 57(1):323-332.
Holderbach et al. Biol. Psych., Published online Dec. 2006, vol. 62, pp. 92-100.
Johnson, et al. (1990) "Neuropharmacolgy of Phencyclidine: Basic Mechanisms and Therapeutic Potential," *Annu. Rev. Pharmacol. Toxicol.*, Vo. 30, pp. 707-750.
Khasanov et al. (2004) "Novel Asymmetric Approach to Proline-Derived Spiro-beta-lactams," *J. Org. Chem.*, 69(17):5766-5769.
Kloog et al. (1988) "Kinetic Characterization of the Phencyclidine-N-Methyl-d-asparate Receptor Interaction: Evidence for a Steric Blockade of the Channel," *Biochemistry*, vol. 27, Issue 3, pp. 843-848.
Kloog et al. (1988) "Mode of Binding of [3H]dibenzocycloalkenimine (MK-801) to the N-methyl-D-aspartate (NMDA) Receptor and its Therapeutic Implication," FEBS Lett., vol. 230, Issue 1-2, pp. 167-170.
Koller et al. (2010) "Novel N-Methyl-D-aspartate Receptor Antagonists: A Review of Compounds Patented Since 2006," *Expert Opin. Ther. Patents*, 20(12):1683-1702.
Kroes et al. (2006) "Development of a Novel Glycobiologic Therapy for Glioblastoma," Neuro-oncol. 8(4):397-398, Oct. 2006, Abstract CB-14, 2 pages.
Kroes et al. (2006) "Development of a Novel Glycobiology-Based Therapeutic for Glioblastoma," *J. Neurochem.*, 99(Suppl. 1):17, Nov. 10, 2006, Abstract 50, 1 page.

Leander et al. (2010) "Lack of Ketamine-Like Discriminative Effects of GLYX-13: A Novel NMDA Receptor Glycine Site Functional Partial Agonist with Antidepressant-Like Preclinical Effects," ACNP, Dec. 2010, 218 (1 page.).
Lynch et al. (2006) "Synaptic Pasticity in Early Aging," *Aging Research Reviews*, vol. 5, pp. 255-280.
Mayer et al. (1990) "Excitatory Amino Acid Receptors, Second Messengers and Regulation of Intracellular Ca2+ in Mammalian Neurons," *Trends in Pharmacol. Sci.*, vol. 11, pp. 254-260.
Mishra et al. (2002) "Three-Dimensional Quantitative Structure-Activity Relationship and Comparative Molecular Field Analysis of Dipeptide Hydroxamic Acid *Helicobacter pylori* Urease Inhibitors," *Antimicrob. Agents and Chemother.*, 46(8):2613-2618.
Monahan et al. (1989) "D-Cycloserine, a Positive Modulator of the N-Methyl-d-Asparate Receptor, Enhances Performance of Learning in Rats," *Pharm. Biochem. Behav.*, vol. 34, pp. 649-653.
Moskal, et al. (2009) "The anti-depressant and anxiolytic properties of GLYX-13: a Glycine-site Functional Partial Agonist (GFPA), a novel mechanism for modulating NMDA receptors," ACNP Annual Meeting, (Dec. 2009) (2 pages) (Abstract).
Moskal et al. (2009) "The Antidepressant and Anxiolytic Properties of GLYX-13: A Novel NMDA Receptor Glycine Site Functional Partial Agonist," (Poster #059) ACNP 2009, Dec. 7, 2009 (1 page).
Moskal et al. (1996) "Monoclonal Antibodies to the Dentate Gyrus: Immunocytochemical Characterization and Flow Cytometric Analysis of Hippocampal Neurons Bearing a Unique Cell-Surface Antigen," *J. Neurosci*, 6(7):2045-2053.
Moskal et al. (2001) "The Use of Antibody Engineering to Create Novel Drugs that Target N-Methyl-D-aspartate Receptors," Current Drug Targets, 2:331-345.
Moskal et al. (2005) "GLYX-13: A Monoclonal Antibody-Derived Peptide that Acts as an N-Methyl-D-aspartate Receptor Modulator," *Neuropharmacology*, 49:1077-1087.
Moskal et al. (2010) "A Novel Approach to Unlocking the Therapeutic Potential of the NMDA Receptor," *Vital Signs e-magazine*, Sep. 2010 (2 pages).
Narahashi et al. (2004) "Mechanisms of Action of Cognitive Enhancers on Neuroreceptors," *Biol. Pharm. Bull.*, Vo. 27, Issue 11, pp. 1701-1706.
Overman et al. (1985) "A Convenient Synthesis of 4-Unsubstituted beta-Lactams," *J. Am. Chem. Sol.*, 107(6):1698-701.
Raghavan et al. (2009) "Allosteric Modulation of the Dopamine D2 Receptor by Pro-Leu-Gly-NH2 Peptidomimetics Constrained in Either a Polyproline II Helix or a Type II beta-Turn Conformation," *J. Med. Chem.*, 52(7):2043-2051.
Ransom et al. (1988) "Cooperative Modulation of [3H]MK-801 Binding to the N-Methyl-d-Asparate Receptor-Ion Channel Complex by I-Glumate, Glycine, and Polyamines," *J. Neurochem*. 51:830-836.
Rasmusson et al. (1973) "6-Substituted Penicillin Derivatives," VI. *Tetrahedron Lett.*, (2):145-8.
Siemion et al. (1988) "Conformational Preferences of the Sequential Fragments of the Hinge Region of the Human IgA1 Immunoglobulin Molecule," *Biophys. Chem.*, 31:35-44.
Stanton et al. (1987) "Inhibition of the Production and Maintenance of Long-Term Potentiation in Rat Hippocampal Slices by a Monoclonal Antibody," *Proc. Natl. Acad. Sci. USA*, 84:1684-1688.
Stanton et al. (2009) "Neuroprotection by a Novel NMDAR Functional Glycine Site Partial Agonist, GLYX-13," *Neuropharmacology and Neurotoxicology NeuroReport*, 00(00):1-5.
Tanwar et al. (2002) "Gene Expression Microarray Analysis Reveals YLK-40 to be a Potential Serum Marker for Malignant Character in Human Glioma," *Cancer Res.*, 62:4364-4368.
Thompson et al. (1992) "Hippocampus-Dependent Learning Facilitated by a Monoclonal Antibody or D-Cycloserine," *Nature*, 359:638-641.
Turturro et al. (1999) "Growth Curves and Survival Characteristics of the Animals Used in the Biomarkers of Aging Program," *Journal of Gerontology: Biological Sciences*, vol. 54A, No. 11, pp. B492-B501.
Wood (2005) "The NMDA Receptor Complex: A Long and Winding Road to Therapeutics," IDrugs, 8(3):229-235.
Wood et al. (2008) "Antinociceptive Action of GLYX-13: An N-Methyl-D-aspartate Receptor Glycine Site Partial Agonist," *NeuroReport*, 19(10):1061-1063.

(56) References Cited

OTHER PUBLICATIONS

Wood et al. (1989) "Tetrapeptide Inhibitors of the IgA1 Proteinases from Type I *Neisseria gonorrhoeae*," *J. Med. Chem.* 32:2407-2411.
Zhang et al. (2008) "A NMDA Receptor Glycine Site Partial Agonist, GLYX-13, Simultaneously Enhances LTP and Reduces LTD at Schaffer Collateral-CA1 Synapses in Hippocampus," *Neuropharmacology*, 55:1238-1250.
Alonso et al. (2001) "Spiro-Beta-Lactams as Beta-Turn Mimetics. Design, Synthesis, and NMR Conformational Analysis," *J. Org. Chem.*, 66(19):6333-6338.
Bittermann et al. (2006) "Chirospecific Synthesis of Spirocyclic Beta-Lactams and Their Characterization as Potent Type II beta-Turn Inducing Peptide Mimetics," *J. Org. Chem.*, 71(1):97-102.
Bittermann et al. (2006) "A Highly Practical RCM Approach Towards a Molecular Building Kit of Spirocyclic Reverse Turn Mimics," *Chemistry*, 12(24):6315-6322.
Careri et al. (2003) "Pentacopper(II) 12-Metallacrown-4 Complexes with Alpha- and Beta-Aminohydroxamic Acids in Aqueous Solution: A Reinvestigation," *J. Inorg. Biochem.*, 93(3-4):174-180.
Coates et al. (2005) "Product Class 9: Beta-Lactams," *Science of Synthesis*, 21:609-646.
Cremonesi, et al. (2010) "Enantiomerically Pure Polyheterocyclic Spiro-beta-Lactams from trans-4-Hydroxy-L-proline," *J. Org. Chem.*, 75(6):2010-2017.
Croce et al. (1999) "Reaction of Mesoionic Compounds Deriving from Cyclic N-Acyl-alpha-amino Acids with N-(Phenylmethylene)benzenesulfonamide," *Tetrahedron*, 55(1):201-210.
Croce et al. (1999) "Stereoselective Synthesis of N-Phenylsulfonyl Substituted Spiro-beta-Lactams," *Tetrahedron: Asymmetry*, 10(6):1193-1199.
Database Registry [Online] Chemical Abstracts Service, Columbus, Ohio US; Sep. 28, 2008, XP002668993, Database Accession No. 1053605-89-2.
Database Registry [Online] Chemical Abstracts Service, Columbus, Ohio, US; Jul. 1, 2008 XP002668992, Database Accession No. 1031928-30-9.
del Pozo et al. (2004) "Diastereo- and Enantioselective Synthesis of Novel beta-Lactam-Containing 1,4-Benzodiazepines Through a Ketene-Imine Cycloaddition Reaction," *Eur. J. Org. Chem.*, (3):535-545.
European Search Report for Application No. EP 09 81 5233 completed on Feb. 8, 2012 and dated May 22, 2012.
NCBI Submission NM_173216, 1989, Retrieved from the internet; <URL:http://www.ncbi.nlm.nih.gov/nuccore/27765090>, 5 pages.
Parac-Vogt et al. (2005) "Pentacopper(II) Complexes of alpha-Aminohydroxamic Acids: Uranyl-Induced Conversion of a 12-Metallacrown-4 to a 15-Metallacrown-5," *J. Inorg. Biochem.*, 99(2):497-504.
Johnson et al. (2003) "The Preparation of a Double Metallahelicate Containing 28 Copper Atoms," *Angew. Chem. Int. Ed. Engl.*, 42(5):546-549.
Li et al. (2007) "N-Heterocyclic Carbene Catalyzed Ring Expansion of 4-Formyl-beta-lactams: Synthesis of Succinimide Derivatives," *Org. Lett.*, 9(18):3519-3521.
Macias et al. (2004) "Diastereoselective [2+2]-Cycloaddition Reactions of Unsymmetrical Cyclic Ketenes with Imines: Synthesis of Modified Prolines and Theoretical Study of the Reaction Mechanism," *J. Org. Chem.* 69(21):7004-7012.
Macias et al. (2004) "Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands," *Tetrahedron Lett.*, 45(24):4657-4660.
Macias et al. (2006) "Synthesis of Enantiopure Pyrrolidine-Derived Peptidomimetics and Oligo-beta-peptides via Nucleophilic Ring-Opening of beta-Lactams," *J. Org. Chem.*, 71(20):7721-7730.
NCBI Submission NM_000149, 1990, Retrieved from the internet; <URL:http://www.ncbi.nlm.nih.gov/nuccore/14827705>, 5 pages.
NCBI Submission NM_001276, 1989, Retrieved from the internet; <URL:http://www.ncbi.nlm.nih.gov/nuccore/144226250>, 5 pages.
Abramets et al. (2008) "Neurophysiological and neurochemical aspects of the effects of antidepressants and mood stabilizers," *Neurophysiology, Kluwer Academic Publishers-Plenum Publishers*. 40(1):64-78.
Burgdorf et al. (2012) "GLYX-13, an NMDA Receptor Glycine-Site Functional Partial Agonist, Induces Antidepressant-Like Effects Without Ketamine-Like Side Effects," *Nature*. Accepted Article Preview, doi: 10.1038/npp.2012.246 (46 pages).
Burgdorf et al. (2010) "The Antidepressant and Anxiolytic Properties of GLYX-13: A Novel NMDA Receptor Glycine Site Functional Partial Agonist," *Abstracts of the Annual Meeting of the Society for Neuroscience, Society for Neuroscience*. Jan. 1, 2010 (2 pages).
Extended European Search Report for EP10822514.5 dated Feb. 13, 2013.
Krystal et al. (1999) "NMDA Agonists and Antagonists as Probes of Glutamatergic Dysfunction and Pharmacotherapies in Neuropsychiatric," *Harvard Review of Psychiatry*. 7(3):125-143.
Pittenger et al. (2007) "The NMDA Receptor as a Therapeutic Target in Major Depressive Disorder," *CNS & Neurological Disorders Drugs Targets*. 6(2):101-115.
International Search Report and Written Opinion for PCT/US2011/024583 mailed Jul. 26, 2011, 7 pages.
British Medical Journal. 1980, pp. 1037-1038.
Chilman-Biair et al. Drugs of the Future, 2003, Abstract.
European Search Report for European Application No. EP11761468.5, dated Jun. 12, 2013, 6 pages.
Kulagowski et al. "3'-(Arylmethyl)- and 3'-(aryloxy)-3-phenyl-4-hydroxyquinolin-2(1H)-ones: orally active antagonists of the glycine site on the NMDA receptor" J Med Chem. May 13, 1994; 37(10):1402-5.
Lake et al. "Schizoaffective disorder merges schizophrenia and bipolar disorders as one disease—there is no schizoaffective disorder." Curr. Opin. Psych., 2007, vol. 20, Issue 4, pgs. Abstract.
M.J. Schnell, The N-methyl D-aspartate receptor glycine site and D-serine metabolism: an evolutionary perspective Philos Trans R Soc Lond B Biol Sci. Jun. 29 2004; 359(1446):943-64.
NIMH—Bipolar Disorder. Published online 2013, pp. 1-9.
NIMH Mental Health Institute. Sciences News, 2013, pp. 1-5.
Office Action for U.S. Appl. No. 13/578,189, mailed Oct. 31, 2013.
Stahl, "Novel therapeutics for schizophrenia: targeting glycine modulation of NMDA glutamate receptors" CNS Spectr., 2007, vol. 12, Issue 6, pp. 423-427.
Sugimoto et al. "Evidence for the Involvement og GABAA receptor blockade in convulsions induced by cephalosporins" Neuropharmacology (2003) 45:304-314.

\* cited by examiner

NMDA RECEPTORS MODULATORS AND USES THEREOF

RELATED APPLICATIONS

This application claims priority to 61/550,782, filed Oct. 24, 2011, and is a continuation in part of PCT/US11/24583, filed Feb. 11, 2011, claiming priority to U.S. Ser. No. 61/303,472, filed Feb. 11, 2010; all of which are hereby incorporated by reference in their entireties.

BACKGROUND

An N-methyl-d-aspartate (NMDA) receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

NMDA receptor compounds may exert dual (agonist/antagonist) effect on the NMDA receptor through the allosteric sites. These compounds are typically termed "partial agonists". In the presence of the principal site ligand, a partial agonist will displace some of the ligand and thus decrease $Ca^{++}$ flow through the receptor. In the absence of or lowered level of the principal site ligand, the partial agonist acts to increase $Ca^{++}$ flow through the receptor channel.

A need continues to exist in the art for novel and more specific/potent compounds that are capable of binding the glycine binding site of NMDA receptors, and provide pharmaceutical benefits. In addition, a need continues to exist in the medical arts for an orally deliverable forms of such compounds.

SUMMARY

Provided herein, at least in part, are compounds that are NMDA modulators, for example, partial agonists of NMDA. For example, disclosed herein are compounds represented by the formula: A compound represented by:

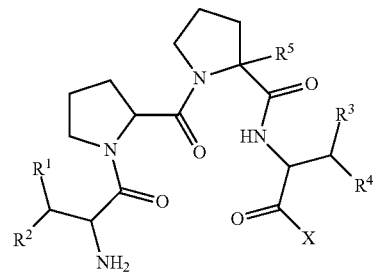

wherein:
and pharmaceutically acceptable salts, stereoisomers, metabolites, and hydrates thereof, wherein: $R^1$, $R^2$, $R^3$, $R^4$, and X are as defined below.

Also provided herein are pharmaceutically acceptable compositions comprising a disclosed compound, and a pharmaceutically acceptable excipient. For example, such compositions may be suitable for oral administration to a patient.

In another aspect, a method of treating a condition selected from the group consisting of depression, Alzheimer's disease, memory loss that accompanies early stage Alzheimer's disease, attention deficit disorder, ADHD, schizophrenia, anxiety, in a patient in need thereof is provided. The method comprises administering to the patient a pharmaceutically effective amount of a disclosed compound and pharmaceutically acceptable salts, stereoisomers, metabolites, and hydrates thereof.

DETAILED DESCRIPTION

This disclosure is generally directed to compounds that are capable of modulating NMDA, e.g., NMDA antagonists or partial agonists, and compositions and/or methods of using the disclosed compounds.

DEFINITIONS

In some embodiments, the compounds, as described herein, may be substituted with any number of substituents or functional moieties. In general, the term "substituted" whether preceded by the term "optionally" or not, and substituents contained in formulas, refer to the replacement of hydrogen radicals in a given structure with the radical of a specified substituent.

In some instances, when more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. In some embodiments, heteroatoms such as nitrogen may have hydrogen substituents and/or any permissible substituents of organic compounds described herein which satisfy the valencies of the heteroatoms. Non-limiting examples of substituents include acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroarylthio; oxo; —F; —Cl; —Br; —I; —OH; —NO$_2$; —N$_3$; —CN; —SCN; —SR$^x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$C(O)R$^x$; —NR$^x$C(O)N(R$^x$)$_2$; —NR$^x$C(O)OR$^x$; —NR$^x$C(NR$^x$)N(R$^x$)$_2$; and —C(R$^x$)$_3$; wherein each occurrence of R$^x$ independently includes, but is not limited to, hydrogen, halogen, acyl, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Furthermore, the compounds described herein are not intended to be limited in any manner by the permissible substituents of organic compounds. In some embodiments, combinations of substituents and variables described herein may be preferably those that result in the formation of stable compounds. The term "stable," as used herein, refers to compounds which possess stability sufficient to allow manufacture and which maintain the integrity of the compound for a sufficient period of time to be detected and preferably for a sufficient period of time to be useful for the purposes detailed herein.

The terms "aryl" and "heteroaryl," as used herein, refer to mono- or polycyclic unsaturated moieties having preferably 3-14 carbon atoms, each of which may be substituted or unsubstituted. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments, "heteroaryl" refers to a mono- or bicyclic heterocyclic ring system having one or two aromatic rings in which one, two, or three ring atoms are heteroatoms independently selected from the group consisting of S, O, and N and the remaining ring atoms are carbon. Non-limiting examples of heteroaryl groups include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "alkyl" as used herein refers to a saturated straight or branched hydrocarbon, for example, such as a straight or branched group of 1-6, 1-4, or 1-3 carbon atom, referred to herein as $C_1$-$C_6$alkyl, $C_1$-$C_4$alkyl, and $C_1$-$C_3$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

Alkyl, alkenyl and alkynyl groups can optionally be substituted, if not indicated otherwise, with one or more groups selected from alkoxy, alkyl, cycloalkyl, amino, halogen, and —C(O)alkyl. In certain embodiments, the alkyl, alkenyl, and alkynyl groups are not substituted, i.e., they are unsubstituted.

The term "amine" or "amino" as used herein refers to a radical of the form —NR$^d$R$^e$, where R$^d$ and R$^e$ are independently selected from hydrogen, alkyl, alkenyl, alkynyl, aryl, arylalkyl, cycloalkyl, haloalkyl, heteroaryl, and heterocyclyl. The amino also may be cyclic, for example, R$^d$ and R$^e$ are joined together with the N to form a 3- to 12-membered ring, e.g., morpholino or piperidinyl. The term amino also includes the corresponding quaternary ammonium salt of any amino group, e.g., —[N(R$^d$)(R$^e$)(R$^f$)]+. Exemplary amino groups include aminoalkyl groups, wherein at least one of R$^d$, R$^e$, or R$^f$ is an alkyl group. In certain embodiment, R$^d$ and R$^e$ are hydrogen or alkyl.

The terms "halo" or "halogen" or "Hal" as used herein refer to F, Cl, Br, or I. The term "haloalkyl" as used herein refers to an alkyl group substituted with one or more halogen atoms.

The terms "heterocyclyl" or "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. The heterocyclic ring may be substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclic group is not substituted, i.e., the heterocyclic group is unsubstituted.

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. "For human administration, preparations should meet sterility, pyrogenicity, general safety and purity standards as required by FDA Office of Biologics standards.

As used in the present disclosure, the term "partial NMDA receptor agonist" is defined as a compound that is capable of binding to a glycine binding site of an NMDA receptor; at low concentrations a NMDA receptor agonist acts substantially as agonist and at high concentrations it acts substantially as an antagonist. These concentrations are experimentally determined for each and every "partial agonist.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ⸺ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

As used in the present disclosure, "NMDA" is defined as N-methyl-d-aspartate.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in defined as that amount needed to give maximal enhancement of a behavior (for example, learning), physiological response (for example, LTP induction), or inhibition of neuropathic pain.

Compounds

Disclosed compounds include those represented by the formula:

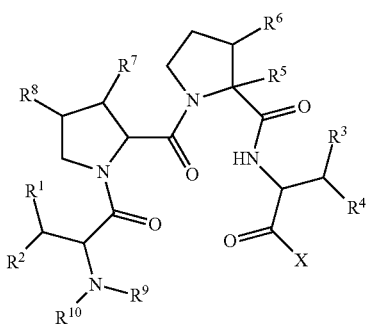

and pharmaceutically acceptable salts, stereoisomers, metabolites, and hydrates thereof, wherein:

$R^1$, $R^2$, $R^3$, and $R^4$ may be independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^x$; —$NO_2$; —$N_3$; —CN; —SCN; —$SR^x$; —C(O)$R^x$; —$CO_2(R^x)$; —C(O)N($R^x$)$_2$; —C(N$R^x$)N($R^x$)$_2$; —OC(O)$R^x$; —$OCO_2R^x$; —OC(O)N($R^x$)$_2$; —N($R^x$)$_2$; —$SOR^x$; —S(O)$_2R^x$; —N$R^x$C(O)$R^x$; —N$R^x$C(O)N($R^x$)$_2$; —N$R^x$C(O)O$R^x$; —N$R^x$C(N$R^x$)N($R^x$)$_2$; and —C($R^x$)$_3$; wherein each occurrence of $R^x$ is independently selected from the group consisting of hydrogen; halogen; acyl; optionally substituted aliphatic; optionally substituted heteroaliphatic; optionally substituted aryl; and optionally substituted heteroaryl;

$R^5$ and $R^6$ may be independently selected from the group consisting of -Q-Ar and hydrogen, provided that at least one of $R^5$ and $R^6$ is -Q-Ar; wherein Q is independently selected from the group consisting of cyclic or acyclic, substituted or unsubstituted, branched or unbranched aliphatic; cyclic or acyclic, substituted or unsubstituted, branched or unbranched heteroaliphatic; and a bond; and wherein Ar is selected from the group consisting substituted or unsubstituted aryl, and substituted or unsubstituted heteroaryl; or $R^5$ and $R^6$, together with the atoms to which they are attached, form a substituted or unsubstituted 4-6 membered heterocyclic or cycloalkyl ring;

$R^7$ and $R^8$ may be independently selected from the group consisting of hydrogen; halogen; hydroxyl; substituted or unsubstituted $C_1$-$C_6$ alkyl; substituted or unsubstituted $C_1$-$C_6$ alkoxy; and substituted or unsubstituted aryl; or $R^7$ and $R^8$, together with the atoms to which they are attached, form a substituted or unsubstituted 4-6 membered heterocyclic or cycloalkyl ring;

$R^9$ and $R^{10}$ may be independently selected from the group consisting of hydrogen; $C_1$-$C_6$ alkyl, optionally substituted by one or more substituents each independently selected from the group consisting of halogen, oxo, and hydroxyl; $C_{2-6}$alkenyl, optionally substituted by one or more substituents each independently selected from the group consisting of halogen, oxo, and hydroxyl; $C_{2-6}$alkynyl, optionally substituted by one or more substituents each independently selected from the group consisting of halogen, oxo, and hydroxyl; $C_{3-6}$cycloalkyl, optionally substituted by one or more substituents each independently selected from the group consisting of $C_{1-6}$alkyl, halogen, oxo, and hydroxyl; phenyl, optionally substituted by one or more substituents each independently selected from the group consisting of $C_{1-6}$alkyl; $C_{1-6}$alkoxy; halogen; hydroxyl; —C(O)$R^x$; —$CO_2(R^x)$; —C(O)N($R^x$)$_2$; —C(N$R^x$)N($R^x$)$_2$; and —C($R^x$)$_3$;

X is selected from the group consisting of $OR^x$ or $NR^xR^x$; wherein each occurrence of $R^x$ is independently selected from the group consisting of hydrogen; halogen; $C_{1-6}$alkyl; $C_{2-6}$alkenyl; $C_{2-6}$alkynyl; $C_{3-6}$cycloalkyl; and phenyl; or $R^9$ and $R^{10}$, together with N, form a 4-6 membered heterocyclic ring, optionally substituted by one or more substituents each independently selected from the group consisting of $C_{1-6}$alkyl, halogen, oxo, and hydroxyl.

In some embodiments, $R^1$, $R^2$, $R^3$, and $R^4$ may be independently selected from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; —$OR^x$; —$NO_2$; —$N_3$; —CN; —SCN; —$SR^x$; —C(O)$R^x$; —$CO_2(R^x)$; —C(O)N($R^x$)$_2$; —C(N$R^x$)N($R^x$)$_2$; —OC(O)$R^x$; —$OCO_2R^x$; —OC(O)N($R^x$)$_2$; —N($R^x$)$_2$; —$SOR^x$; —S(O)$_2R^x$; —N$R^x$C(O)$R^x$; —N$R^x$C(O)N($R^x$)$_2$; —N$R^x$C(O)O$R^x$; —N$R^x$C(N$R^x$)N($R^x$)$_2$; and —C($R^x$)$_3$; wherein heteroaryl is a 5-6 membered ring having one, two, or three heteroatoms each independently selected from N, O, or S; wherein heteroaryl is optionally substituted with one or more substituents each independently selected from $R^b$; wherein heterocyclyl is a 4-7 membered ring optionally substituted by one or more substituents each independently selected from $R^c$; wherein when heterocyclyl contains a —NH— moiety, that —NH— moiety is optionally substituted by $R^d$; wherein $C_{2-6}$alkenyl and $C_{2-6}$alkynyl, are each independently optionally substituted by one or more substituents each independently selected from $R^e$; wherein $C_{1-6}$alkyl is optionally substituted by one or more substituents each independently selected from $R^f$; wherein $C_{3-6}$cycloalkyl is independently optionally substituted by one or more substituents each independently selected from $R^g$;

$R^b$ may be selected, independently for each occurrence, from the group consisting of halogen; hydroxyl; —$NO_2$; —$N_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cyclo alkyl-$C_{1-6}$alkyl-; $C_{1-6}$alkoxycarbonyl-N($R^a$)—; $C_{1-6}$alkylN($R^a$)—; $C_{1-6}$alkyl- N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and C$_{1-6}$alkyl-carbonyl-N(R$^a$)—;

R$^a$ and R$^{a'}$ may be selected, independently for each occurrence, from the group consisting of hydrogen and C$_{1-6}$alkyl, or R$^a$ and R$^{a'}$ when taken together with the nitrogen to which they are attached form a 4-6 membered heterocyclic ring, wherein C$_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

R$^c$ may be selected, independently for each occurrence, from the group consisting of halogen; hydroxyl; —NO$_2$; —N$_3$; —CN; —SCN; oxo; C$_{1-6}$alkyl; C$_{2-6}$alkenyl; C$_{2-6}$alkynyl; C$_{3-6}$cycloalkyl; C$_{1-6}$alkoxy; C$_{3-6}$alkenyloxy; C$_{3-6}$alkynyloxy; C$_{3-6}$cycloalkoxy; C$_{1-6}$alkyl-S(O)$_w$—, where w is 0, 1, or 2; C$_{1-6}$alkylC$_{3-6}$cycloalkyl-; C$_{3-6}$cyclo alkyl-C$_{1-6}$alkyl-; C$_{1-6}$alkoxycarbonyl-N(R$^a$)—; C$_{1-6}$alkylN(R$^a$)—; C$_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and C$_{1-6}$alkyl-carbonyl-N(R$^a$)—;

R$^d$ may be selected, independently for each occurrence, from the group consisting of C$_{1-6}$alkyl, C$_{1-6}$alkylcarbonyl, and C$_{1-6}$alkylsulfonyl, wherein C$_{1-6}$alkyl is optionally substituted by one or more substituents each independently selected from halogen, hydroxyl, and R$^a$R$^{a'}$N—;

R$^e$ may be selected, independently for each occurrence, from the group consisting of halogen; hydroxyl; —NO$_2$; —N$_3$; —CN; —SCN; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2;

R$^f$ may be selected, independently for each occurrence, from the group consisting of halogen; hydroxyl; —NO$_2$; —N$_3$; —CN; —SCN; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2;

R$^g$ may be selected, independently for each occurrence, from the group consisting of halogen, hydroxyl, —NO$_2$; —N$_3$; —CN; —SCN; C$_{1-6}$alkyl; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2;

R$^x$ may be selected, independently, from the group consisting of hydrogen; halogen; C$_{1-6}$alkyl; C$_{2-6}$alkenyl; C$_{2-6}$alkynyl; C$_{3-6}$cycloalkyl; phenyl; naphthyl; heteroaryl; heterocyclyl; C$_{3-6}$cycloalkyl-C$_{1-6}$alkyl-; phenyl-C$_{1-6}$alkyl-; naphthyl-C$_{1-6}$alkyl-; heteroaryl-C$_{1-6}$alkyl-; and heterocyclyl-C$_{1-6}$alkyl-; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein C$_{2-6}$alkenyl and C$_{2-6}$alkynyl, are each independently optionally substituted by one or more substituents each independently selected from R$^e$; wherein C$_{1-6}$alkyl is optionally substituted by one or more substituents each independently selected from R$^f$; wherein C$_{3-6}$cycloalkyl is independently optionally substituted by one or more substituents each independently selected from R$^g$.

In certain embodiments, at least one of R$^1$, R$^2$, R$^3$, and R$^4$ may be hydroxyl.

In some instances, at least one of R$^1$, R$^2$, R$^3$, and R$^4$ may be C$_1$-C$_6$ alkyl, optionally substituted with one, two, or three substituents selected independently from the group consisting of halogen, hydroxyl, —NH$_2$, and cyano.

In some embodiments, at least one of R$^5$ and R$^6$ may be —(C$_1$-C$_6$ alkylene)-Ar. At least one of R$^5$ and R$^6$ may also be —CH$_2$—Ar. In some cases, at least one of R$^5$ and R$^6$ is -Q-phenyl. In certain examples, one of R$^5$ and R$^6$ may be hydrogen.

In some cases, R$^7$ and R$^8$ may be independently selected from the group consisting of hydrogen; halogen; hydroxyl; C$_1$-C$_6$ alkyl; phenyl; and naphthyl; or R$^7$ and R$^8$, together with the atoms to which they are attached, form a 4-6 membered heterocyclic or cycloalkyl ring; wherein C$_1$-C$_6$ alkyl, phenyl, naphthyl, the cycloalkyl ring, and the heterocyclic ring each may be substituted independently by one or more substituents selected from the group consisting of halogen; hydroxyl; —NO$_2$; —N$_3$; —CN; —SCN; C$_{1-4}$alkoxy; C$_{1-4}$alkoxycarbonyl; R$^a$R$^{a'}$N—; R$^a$R$^{a'}$N-carbonyl; R$^a$R$^{a'}$N—SO$_2$—; and C$_{1-4}$alkylS(O)$_w$—, where w is 0, 1, or 2; wherein R$^a$ and R$^{a'}$ may be selected, independently for each occurrence, from the group consisting of hydrogen and C$_{1-6}$alkyl, or R$^a$ and R$^{a'}$ when taken together with the nitrogen to which they are attached form a 4-6 membered heterocyclic ring, wherein C$_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl.

In some cases, R$^7$ and R$^8$ may be hydrogen.

X may be, for example, selected from the group consisting of OH and NH$_2$.

In an exemplary embodiment, a compound may be represented by:

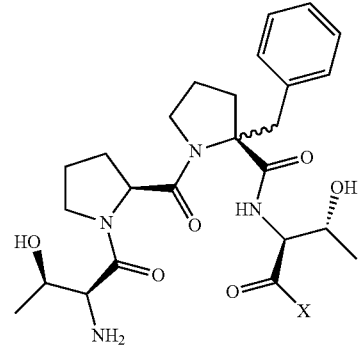

wherein X is OH or NH$_2$.

In an exemplary embodiment, a compound may be represented by:

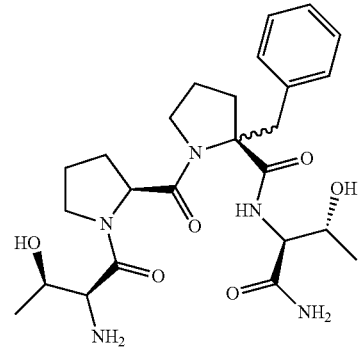

In another exemplary embodiment, a compound may be represented by:

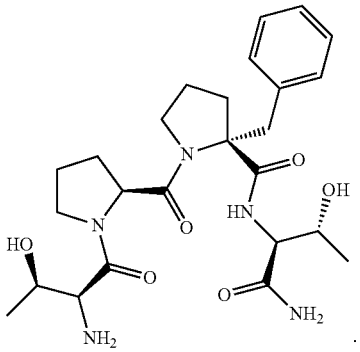

In yet another exemplary embodiment, a compound may be represented by:

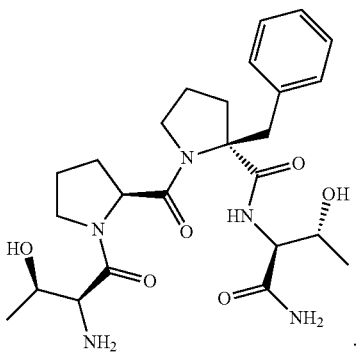 [SMILES: C[C@@H](O)[C@H](N)C(=O)N1CCC[C@H]1C(=O)N1CCC[C@]1(Cc1ccccc1)C(=O)N[C@H](C(N)=O)[C@@H](C)O]

Provided herein, for example, is a compound represented by:

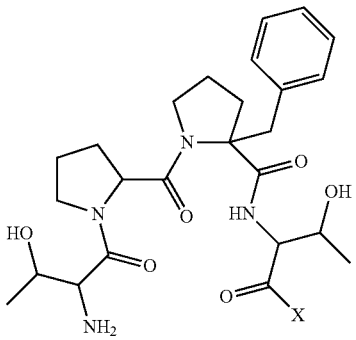

wherein X is OH or NH$_2$, and pharmaceutically acceptable salts thereof.

Disclosed compounds also include those represented by the formula:

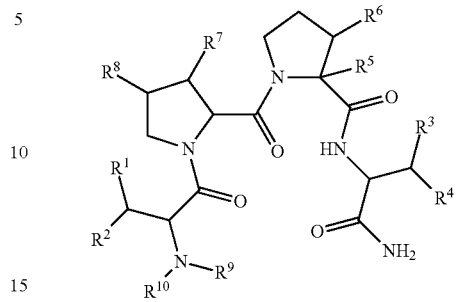

and pharmaceutically acceptable salts, stereoisomers, metabolites, and hydrates thereof, wherein:

$R^1$ and $R^3$ may be independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^x$; —NO$_2$; —N$_3$; —CN; —SCN; —SR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$C(O)R$^x$; —NR$^x$C(O)N(R$^x$)$_2$; —NR$^x$C(O)OR$^x$; —NR$^x$C(NR$^x$)N(R$^x$)$_2$; and —C(R$^x$)$_3$; wherein each occurrence of R$^x$ is independently selected from the group consisting of hydrogen; halogen; acyl; optionally substituted aliphatic; optionally substituted heteroaliphatic; optionally substituted aryl; and optionally substituted heteroaryl;

$R^2$ and $R^4$ may be independently selected from the group consisting of hydrogen and —OR$^x$, provided that at least one of $R^2$ and $R^4$ is hydrogen, wherein R$^x$ is selected from the group consisting of hydrogen; halogen; acyl; optionally substituted aliphatic; optionally substituted heteroaliphatic; optionally substituted aryl; and optionally substituted heteroaryl;

$R^5$ and $R^6$ may be independently selected from the group consisting of -Q-Ar and hydrogen; wherein Q is independently selected from the group consisting of cyclic or acyclic, substituted or unsubstituted, branched or unbranched aliphatic; cyclic or acyclic, substituted or unsubstituted, branched or unbranched heteroaliphatic; and a bond; and wherein Ar is selected from the group consisting substituted or unsubstituted aryl, and substituted or unsubstituted heteroaryl; or $R^5$ and $R^6$, together with the atoms to which they are attached, form a substituted or unsubstituted 4-6 membered heterocyclic or cycloalkyl ring;

$R^7$ and $R^8$ are independently selected from the group consisting of hydrogen; halogen; hydroxyl; substituted or unsubstituted $C_1$-$C_6$ alkyl; substituted or unsubstituted $C_1$-$C_6$ alkoxy; and substituted or unsubstituted aryl; or $R^7$ and $R^8$, together with the atoms to which they are attached, form a substituted or unsubstituted 4-6 membered heterocyclic or cycloalkyl ring;

$R^9$ and $R^{10}$ may be independently selected from the group consisting of hydrogen; $C_1$-$C_6$ alkyl, optionally substituted by one or more substituents each independently selected from the group consisting of halogen, oxo, and hydroxyl; $C_{2-6}$alkenyl, optionally substituted by one or more substituents each independently selected from the group consisting of halogen, oxo, and hydroxyl; $C_{2-6}$alkynyl, optionally substituted by one or more substituents each independently selected from the group consisting of halogen, oxo, and hydroxyl; $C_{3-6}$cycloalkyl, optionally substituted by one or more substituents each independently selected from the group consisting of $C_{1-6}$alkyl, halogen, oxo, and hydroxyl; phenyl, optionally substituted by one or more substituents each independently selected from the group consisting of $C_{1-6}$alkyl; $C_{1-6}$alkoxy; halogen; hydroxyl; —C(O)R$^x$; —CO$_2$(R$^x$); —C(O)N(R$^x$)$_2$; —C(NR$^x$)N(R$^x$)$_2$; and —C(R$^x$)$_3$; wherein each occurrence of R$^x$ is independently selected from the group consisting of hydrogen; halogen; $C_{1-6}$alkyl; $C_{2-6}$alkenyl; $C_{2-6}$alkynyl; $C_{3-6}$cycloalkyl; and phenyl; or R$^9$ and R$^{10}$, together with N, form a 4-6 membered heterocyclic ring, optionally substituted by one or more substituents each independently selected from the group consisting of $C_{1-6}$alkyl, halogen, oxo, and hydroxyl.

In some embodiments, R$^1$ and R$^3$ may be independently selected from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; —OR$^x$; —NO$_2$; —N$_3$; —CN; —SCN; —SR$^x$; —C(O)R$^x$; —CO$_2$(R$^x$); —C(O)N(R$^x$)$_2$; —C(NR$^x$)N(R$^x$)$_2$; —OC(O)R$^x$; —OCO$_2$R$^x$; —OC(O)N(R$^x$)$_2$; —N(R$^x$)$_2$; —SOR$^x$; —S(O)$_2$R$^x$; —NR$^x$C(O)R$^x$; —NR$^x$C(O)N(R$^x$)$_2$; —NR$^x$C(O)OR$^x$; —NR$^x$C(NR$^x$)N(R$^x$)$_2$; and —C(R$^x$)$_3$; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein $C_{2-6}$alkenyl and $C_{2-6}$alkynyl, are each independently optionally substituted by one or more substituents each independently selected from R$^e$; wherein $C_{1-6}$alkyl is optionally substituted by one or more substituents each independently selected from R$^f$; wherein $C_{3-6}$cycloalkyl is independently optionally substituted by one or more substituents each independently selected from R$^g$;

R$^b$ may be selected, independently for each occurrence, from the group consisting of halogen; hydroxyl; —NO$_2$; —N$_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cycloalkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^a$ and R$^{a'}$ may be selected, independently for each occurrence, from the group consisting of hydrogen and $C_{1-6}$alkyl, or R$^a$ and R$^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

R$^c$ may be selected, independently for each occurrence, from the group consisting of halogen; hydroxyl; —NO$_2$; —N$_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkyl$C_{3-6}$cycloalkyl-; $C_{3-6}$cyclo alkyl-$C_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and R$^a$R$^{a'}$N—;

R$^e$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^f$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^g$ may be selected, independently for each occurrence, from the group consisting of halogen, hydroxyl, —NO$_2$; —N$_3$; —CN; —SCN; $C_{1-6}$alkyl; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^x$ may be selected, independently, from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein $C_{2-6}$alkenyl and $C_{2-6}$alkynyl, are each independently optionally substituted by one or more substituents each independently selected from R$^e$; wherein $C_{1-6}$alkyl is optionally substituted by one or more substituents each independently selected from R$^f$; wherein $C_{3-6}$cycloalkyl is independently optionally substituted by one or more substituents each independently selected from R$^g$.

In some cases, R$^2$ and R$^4$ may be independently selected from the group consisting of hydrogen and —OR$^x$, provided that at least one of R$^2$ and R$^4$ is hydrogen, wherein R$^x$ may be selected from the group consisting of hydrogen; halogen; $C_{1-6}$alkyl; $C_{2-6}$alkenyl; $C_{2-6}$alkynyl; $C_{3-6}$cycloalkyl; phenyl; naphthyl; heteroaryl; heterocyclyl; $C_{3-6}$cycloalkyl-$C_{1-6}$alkyl-; phenyl-$C_{1-6}$alkyl-; naphthyl-$C_{1-6}$alkyl-; heteroaryl-$C_{1-6}$alkyl-; and heterocyclyl-$C_{1-6}$alkyl-; wherein heteroaryl is a 5-6 membered ring having one, two, or three heteroatoms each independently selected from N, O, or S; wherein heteroaryl is optionally substituted with one or more substituents each independently selected from R$^b$; wherein heterocyclyl is a 4-7 membered ring optionally substituted by one or more substituents each independently selected from R$^c$; wherein when heterocyclyl contains a —NH— moiety, that —NH— moiety is optionally substituted by R$^d$; wherein $C_{2-6}$alkenyl and $C_{2-6}$alkynyl, are each independently optionally substituted by one or more substituents each independently selected from R$^e$; wherein $C_{1-6}$alkyl is optionally substituted by one or more substituents each independently selected from R$^f$; wherein $C_{3-6}$cycloalkyl is independently optionally substituted by one or more substituents each independently selected from R$^g$;

R$^b$ may be selected, independently for each occurrence, from the group consisting of halogen; hydroxyl; —NO$_2$; —N$_3$; —CN; —SCN; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkylC$_{3-6}$cycloalkyl-; $C_{3-6}$cycloalkyl-C$_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^a$ and R$^{a'}$ may be selected, independently for each occurrence, from the group consisting of hydrogen and $C_{1-6}$alkyl, or R$^a$ and R$^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

R$^c$ may be selected, independently for each occurrence, from the group consisting of halogen; hydroxyl; —NO$_2$; —N$_3$; —CN; —SCN; oxo; $C_{1-6}$alkyl; $C_{2-6}$alkenyl; $C_{2-6}$alkynyl; $C_{3-6}$cycloalkyl; $C_{1-6}$alkoxy; $C_{3-6}$alkenyloxy; $C_{3-6}$alkynyloxy; $C_{3-6}$cycloalkoxy; $C_{1-6}$alkyl-S(O)$_w$—, where w is 0, 1, or 2; $C_{1-6}$alkylC$_{3-6}$cycloalkyl-; $C_{3-6}$cyclo alkyl-C$_{1-6}$alkyl-; $C_{1-6}$alkoxycarbonyl-N(R$^a$)—; $C_{1-6}$alkylN(R$^a$)—; $C_{1-6}$alkyl-N(R$^a$)carbonyl-; R$^a$R$^{a'}$N—; R$^a$R$^{a'}$N-carbonyl-; R$^a$R$^{a'}$N-carbonyl-N(R$^a$)—; R$^a$R$^{a'}$N—SO$_2$—; and $C_{1-6}$alkyl-carbonyl-N(R$^a$)—;

R$^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and R$^a$R$^{a'}$N—;

R$^e$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^f$ may be selected, independently for each occurrence, from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2;

R$^g$ may be selected, independently for each occurrence, from the group consisting of halogen, hydroxyl, —NO$_2$; —N$_3$; —CN; —SCN; $C_{1-6}$alkyl; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2.

In certain embodiments, R$^5$ and R$^6$ may be independently selected from the group consisting of -Q-Ar and hydrogen; wherein Q is independently selected from the group consisting of $C_{1-6}$alkyl; $C_{2-6}$alkenyl; $C_{2-6}$alkynyl; $C_{3-6}$cycloalkyl; heterocyclyl; $C_{3-6}$cycloalkyl-C$_{1-6}$alkyl-; heterocyclyl-C$_{1-6}$alkyl-; and a bond; and wherein Ar is selected from the group consisting substituted or unsubstituted phenyl, naphthyl, and heteroaryl; or R$^5$ and R$^6$, together with the atoms to which they are attached, form a 4-6 membered heterocyclic or cycloalkyl ring, optionally substituted by one or more substituents each independently selected from halogen, hydroxyl, —NO$_2$; —N$_3$; —CN; —SCN; $C_{1-6}$alkyl; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2; and wherein R$^a$ and R$^{a'}$ may be selected, independently for each occurrence, from the group consisting of hydrogen and $C_{1-6}$alkyl, or R$^a$ and R$^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl.

In certain embodiments, at least one of R$^1$, R$^2$, R$^3$, and R$^4$ may be hydroxyl.

In some instances, at least one of R$^1$, R$^2$, R$^3$, and R$^4$ may be $C_1$-$C_6$ alkyl, optionally substituted with one, two, or three substituents selected independently from the group consisting of halogen, hydroxyl, —NH$_2$, and cyano.

In some embodiments, at least one of R$^5$ and R$^6$ may be —(C$_1$-C$_6$ alkylene)-Ar. At least one of R$^5$ and R$^6$ may also be —CH$_2$—Ar. In some cases, at least one of R$^5$ and R$^6$ is -Q-phenyl. In certain examples, one of R$^5$ and R$^6$ may be hydrogen.

In some cases, R$^7$ and R$^8$ may be independently selected from the group consisting of hydrogen; halogen; hydroxyl; $C_1$-$C_6$ alkyl; phenyl; and naphthyl; or R$^7$ and R$^8$, together with the atoms to which they are attached, form a 4-6 membered heterocyclic or cycloalkyl ring; wherein $C_1$-$C_6$ alkyl, phenyl, naphthyl, the cycloalkyl ring, and the heterocyclic ring each may be substituted independently by one or more substituents selected from the group consisting of halogen; hydroxyl; —NO$_2$; —N$_3$; —CN; —SCN; $C_{1-4}$alkoxy; $C_{1-4}$alkoxycarbonyl; R$^a$R$^{a'}$N—; R$^a$R$^{a'}$N-carbonyl; R$^a$R$^{a'}$N—SO$_2$—; and $C_{1-4}$alkylS(O)$_w$—, where w is 0, 1, or 2; wherein R$^a$ and R$^{a'}$ may be selected, independently for each occurrence, from the group consisting of hydrogen and $C_{1-6}$alkyl, or R$^a$ and R$^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl.

In some cases, R$^7$ and R$^8$ may be hydrogen.

In an exemplary embodiment, a compound may be represented by:

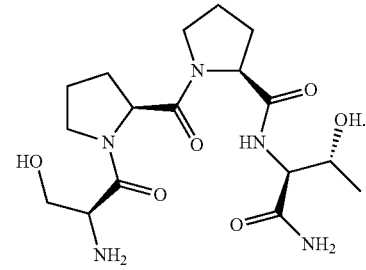 [SMILES: C[C@@H](O)[C@H](NC(=O)[C@@H]1CCCN1C(=O)[C@@H]1CCCN1C(=O)[C@@H](N)CO)C(N)=O]

In another exemplary embodiment, a compound may be represented by:

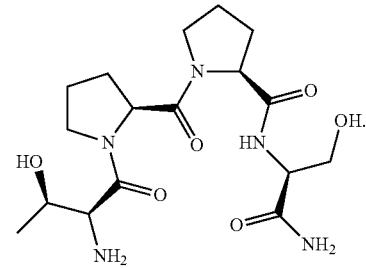 [SMILES: C[C@@H](O)[C@H](N)C(=O)N1CCC[C@H]1C(=O)N1CCC[C@H]1C(=O)N[C@@H](CO)C(N)=O]

In yet another exemplary embodiment, a compound may be represented by:

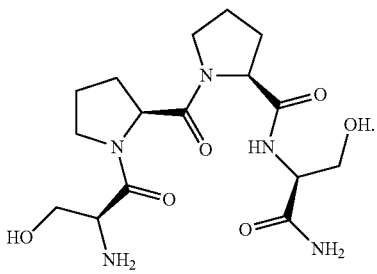 [SMILES: NC(=O)[C@H](CO)NC(=O)[C@@H]1CCCN1C(=O)[C@@H]1CCCN1C(=O)[C@@H](N)CO]

For example, provided herein is a compound represented by:

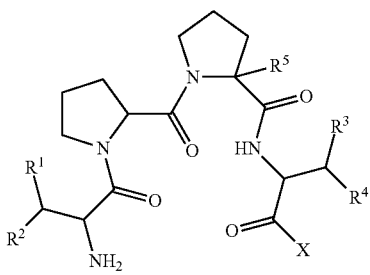

wherein:

$R^1$, $R^2$, $R^3$, and $R^4$ are each independently selected from the group consisting of hydrogen; halogen, $C_1$-$C_6$alkyl, or —OH;

$R^5$ is selected from the group consisting of —$CH_2$-phenyl and hydrogen, provided that $R^5$ is —$CH_2$-phenyl when $R_1$ and $R_3$ are —OH and $R_2$ and $R_4$ are methyl;

X is selected from the group consisting of $OR^x$ and $NR^xR^x$, wherein $R^x$ is independently selected, for each occurrence, from the group consisting of hydrogen, and $C_1$-$C_6$alkyl; and pharmaceutically acceptable salts, stereoisomers, and hydrates thereof.

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50, between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or S) may possess enhanced therapeutic characteristic relative to racemic formulations of a disclosed compounds or mixture of compounds.

Disclosed compounds may provide for efficient cation channel opening at the NMDA receptor, e.g. may bind or associate with the glutamate site of the NMDA receptor to assist in opening the cation channel. The disclosed compounds may be used to regulate (turn on or turn off) the NMDA receptor through action as an agonist.

The compounds as described herein may be glycine site NMDA receptor partial agonists. A partial agonist as used in this context will be understood to mean that at a low concentration, the analog acts as an agonist and at a high concentration, the analog acts as an antagonist. Glycine binding is not inhibited by glutamate or by competitive inhibitors of glutamate, and also does not bind at the same site as glutamate on the NMDA receptor. A second and separate binding site for glycine exists at the NMDA receptor. The ligand-gated ion channel of the NMDA receptor is, thus, under the control of at least these two distinct allosteric sites. Disclosed compounds may be capable of binding or associating with the glycine binding site of the NMDA receptor. In some embodiments, disclosed compounds may possess a potency that is 10-fold or greater than the activity of existing NMDA receptor glycine site partial agonists. For example, disclosed compounds may possess a 10-fold to 20-fold enhanced potency compared to GLYX-13. GLYX-13 is represented by:

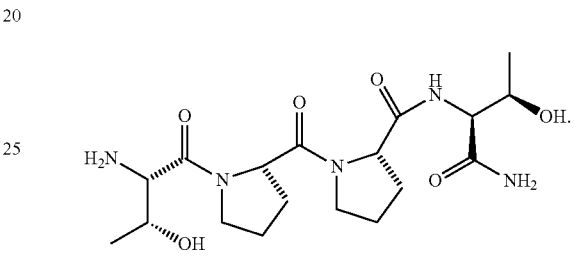

For example, provided herein are compounds that may be at least about 20-fold more potent as compared to GLYX-13, as measured by burst activated NMDA receptor-gated single neuron conductance ($I_{NMDA}$) in a culture of hippocampal CA1 pyramidal neurons at a concentration of 50 nM. In another embodiment, a provided compound may be capable of generating an enhanced single shock evoked NMDA receptor-gated single neuron conductance ($I_{NMDA}$) in hippocampal CA1 pyramidal neurons at concentrations of 100 nM to 1 μM. Disclosed compounds may have enhanced potency as compared to GLYX-13 as measured by magnitude of long term potentiation (LTP) at Schaffer collateral-CA-1 synapses in in vitro hippocampal slices.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=($TD_{50}$):($ED_{50}$). In some embodiments, a disclosed compound may have a therapeutic index of at least about 10:1, at least about 50:1, at least about 100:1, at least about 200:1, at least about 500:1, or at least about 1000:1.

Compositions

In other aspects, formulations and compositions comprising the disclosed compounds and optionally a pharmaceutically acceptable excipient are provided. In some embodiments, a contemplated formulation comprises a racemic mixture of one or more of the disclosed compounds.

Contemplated formulations may be prepared in any of a variety of forms for use. By way of example, and not limitation, the compounds may be prepared in a formulation suitable for oral administration, subcutaneous injection, or other methods for administering an active agent to an animal known in the pharmaceutical arts.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms of the invention are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect of the invention, a compound may be formulated with one or more additional compounds that enhance the solubility of the compound.
Methods Methods for treating cognitive disorders and for enhancing learning are provided. Such methods include administering a pharmaceutically acceptable formulation of one or more of the disclosed compounds to a patient in need thereof. Also contemplated are methods of treating patients suffering from, memory deficits associated with aging, schizophrenia, special learning disorders, seizures, post-stroke convulsions, brain ischemia, hypoglycemia, cardiac arrest, epilepsy, migraine, as well as Huntington's, Parkinson's and Alzheimer's disease.

Other methods contemplated include the treatment of cerebral ischemia, stroke, brain trauma, brain tumors, acute neuropathic pain, chronic neuropathic pain, sleep disorders, drug addiction, depression, certain vision disorders, ethanol withdrawal, anxiety, memory and learning disabilities, autism, epilepsy, AIDS dementia, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, peripheral neuropathy, myelopathy, ischemic retinopathy, diabetic retinopathy, glaucoma, cardiac arrest, behavior disorders, impulse control disorders, Alzheimer's disease, memory loss that accompanies early stage Alzheimer's disease, attention deficit disorder, ADHD, schizophrenia, amelioration of opiate, nicotine addiction, ethanol addition, traumatic brain injury, spinal cord injury, post-traumatic stress syndrome, and Huntington's chorea.

For example, provided herein is a method of treating depression in a patient need thereof, comprising administering a disclosed compound, e.g by acutely administering a disclosed compound. In certain embodiments, the treatment-resistant patient is identified as one who has been treated with at least two types of antidepressant treatments prior to administration of a disclosed compound. In other embodiments, the treatment-resistant patient is one who is identified as unwilling or unable to tolerate a side effect of at least one type of antidepressant treatment.

The most common depression conditions include Major Depressive Disorder and Dysthymic Disorder. Other depression conditions develop under unique circumstances. Such depression conditions include but are not limited to Psychotic depression, Postpartum depression, Seasonal affective disorder (SAD), mood disorder, depressions caused by chronic medical conditions such as cancer or chronic pain, chemotherapy, chronic stress, post traumatic stress disorders, and Bipolar disorder (or manic depressive disorder).

Refractory depression occurs in patients suffering from depression who are resistant to standard pharmacological treatments, including tricyclic antidepressants, MAOIs, SSRIs, and double and triple uptake inhibitors and/or anxiolytic drugs, as well non-pharmacological treatments such as psychotherapy, electroconvulsive therapy, vagus nerve stimulation and/or transcranial magnetic stimulation. A treatment resistant-patient may be identified as one who fails to experience alleviation of one or more symptoms of depression (e.g., persistent anxious or sad feelings, feelings of helplessness, hopelessness, pessimism) despite undergoing one or more standard pharmacological or non-pharmacological treatment. In certain embodiments, a treatment-resistant patient is one who fails to experience alleviation of one or more symptoms of depression despite undergoing treatment with two different antidepressant drugs. In other embodiments, a treatment-resistant patient is one who fails to experience alleviation of one or more symptoms of depression despite undergoing treatment with four different antidepressant drugs. A treatment-resistant patient may also be identified as one who is unwilling or unable to tolerate the side effects of one or more standard pharmacological or non-pharmacological treatment.

In yet another aspect, a method for enhancing pain relief and for providing analgesia to an animal is provided.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions contemplated herein. Psychotic disorders such as schizoaffective disorders, delusional disorders, brief psychotic disorders, shared psychotic disorders, and psychotic disorders with delusions or hallucinations may also be treated using the compositions contemplated herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present.

Disorganized type schizophrenia may be characterized where thought disorder and flat affect are present together.

Catatonic type schizophrenia may be characterized where the subject may be almost immobile or exhibit agitated, purposeless movement. Symptoms can include catatonic stupor and waxy flexibility.

Undifferentiated type schizophrenia may be characterized where psychotic symptoms are present but the criteria for paranoid, disorganized, or catatonic types have not been met.

Residual type schizophrenia may be characterized where positive symptoms are present at a low intensity only.

Post-schizophrenic depression may be characterized where a depressive episode arises in the aftermath of a schizophrenic illness where some low-level schizophrenic symptoms may still be present.

Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis.

In another embodiment, methods for treating delusions (e.g., "non-bizarre") that may be present in, for example, delusional disorder are provided.

Also provided are methods for treating social withdrawal in conditions including, but not limited to, social anxiety disorder, avoidant personality disorder, and schizotypal personality disorder.

Additionally, methods are provided for treating obsessive-compulsive disorder (OCD).

EXAMPLES

The following examples are provided for illustrative purposes only, and are not intended to limit the scope of the disclosure.

General Methods

All solvents used were of laboratory grade solvents. Tetrahydrofuran was predistilled over KOH and then distilled over Na/benzophenone under argon. Dichloromethane was distilled over CaH2. Diisopropyl amine was distilled over KOH.

Column chromatography was conducted on silica gel 100-200 mesh. For TLC purpose commercially available aluminum backed plates coated with silica gel 60 F254 from Merck, Darmstadt, West Germany were used.

NMR spectra were recorded on a Varian-Unity Inova 500 MHz, and Bruker Avance III 400 MHz instruments. All NMR spectra were determined in deuterated DMSO and chemical shifts are reported as δ values in ppm with tetramethylsilane was an internal standard (δ=0). Coupling constants (J) are given in Hertz. Signals in the $^1$H NMR spectra are characterized as s (singlet), d (doublet), t (triplet), m (multiplet), and br s (broad singlet).

Chemical purities were determined by HPLC on Waters Aquity system by using either aq.TFA/aq.MeCN or aq.NH4OAc/aq.MeCN with a PDA detector. Mass were determined on Schimadzu 2010 EV LCMS system by using either aq.TFA/aq.MeCN or aq.NH4OAc/aq.MeCN with a PDA detector. Chiral purities were determined by using Chiralpak (IA) column (250×4.6 mm, 5 um) on a Agilent-1200 series using n-hexane:ethanol as mobile phase with PDA detector.

Optical rotation were determined in chloroform and water in a 2-mL cell with 50 mm path length on a JASCO P-2000 polarimeter.

Example 1

Synthesis of (S)—N-((2S,3R)-1-amino-3-hydroxy-1-oxobutan-2-yl)-1-((S)-1-((S)-2-amino-3-hydroxypropanoyl)pyrrolidine-2-carbonyl)pyrrolidine-2-carboxamide (Compound A)

The following reaction sequence was used (Scheme A) to synthesize (S)—N-((2S,3R)-1-amino-3-hydroxy-1-oxobutan-2-yl)-1-((S)-1-((S)-2-amino-3-hydroxypropanoyl)pyrrolidine-2-carbonyl)pyrrolidine-2-carboxamide

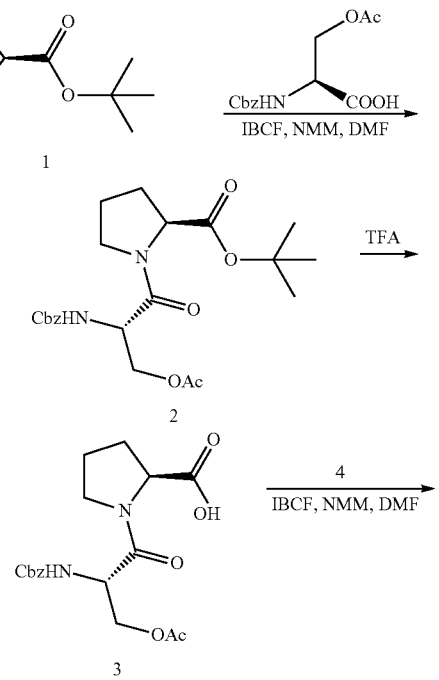

Scheme A. Synthesis of Compound A.

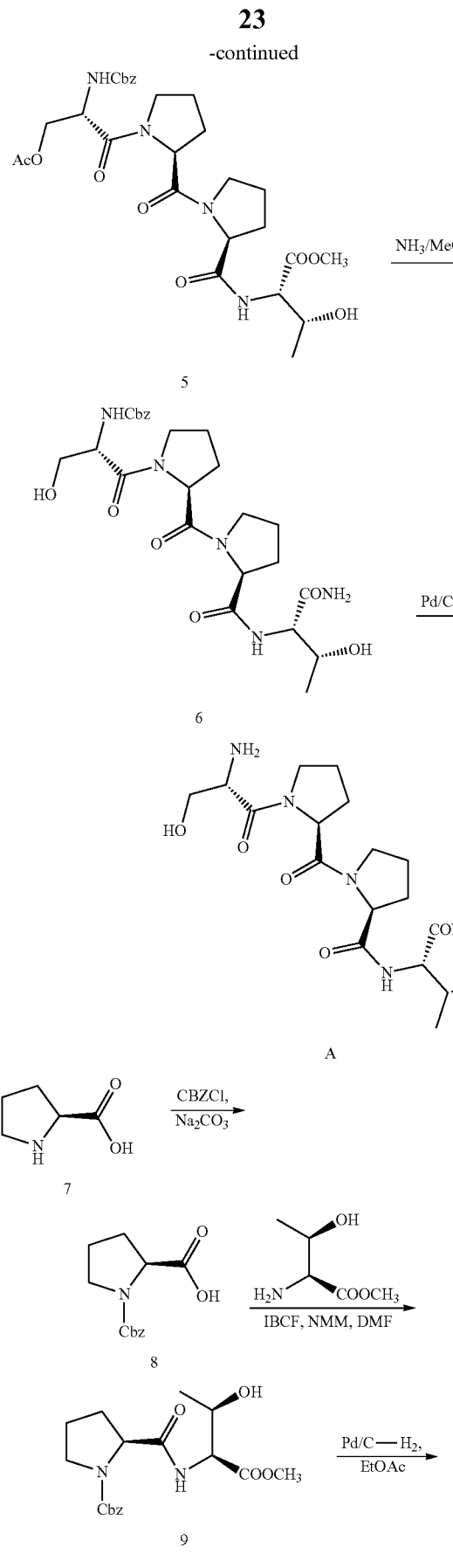

Synthesis of (S)-tert-butyl 1-((S)-3-acetoxy-2-(benzyloxycarbonylamino)-propanoyl)-pyrrolidine-2-carboxylate (2)

(S)-3-Acetoxy-2-(benzyloxycarbonylamino)-propanoic acid (1.5 g, 5.33 mmol) was dissolved in CH₂Cl₂ (15 mL). N-Methylmorpholine (NMM) (0.64 mL, 5.87 mmol) and isobutyl chloroformate (IBCF) (0.72 mL, 6.12 mmol) were added at −15° C. and stirred for 30 minutes under inert atmosphere. A mixture of (S)-tert-butyl pyrrolidine-2-carboxylate (1) (998 mg, 5.87 mmol) and NMM (0.64 mL, 5.87 mmol) in DMF (5 mL) were added drop wise to the reaction mixture and stirring was continued for another 3 h at RT. The reaction mixture was diluted with DCM (200 mL), washed with water (50 mL), citric acid solution (10 mL) and brine (10 mL). The separated organic layer was dried over anhydrous Na₂SO₄ and concentrated under reduced pressure. The obtained crude residue was purified by silica gel column chromatography eluting with 30% EtOAc/Hexane to afford compound 2 (1.6 g, 69.5%).

¹H-NMR: (200 MHz, DMSO-d₆): δ 7.81-7.76 (d, J=20.5 Hz, 1H), 7.35-7.30 (m, 5H), 5.03-4.97 (m, 2H), 4.61-4.55 (m, 1H), 4.32-4.16 (m, 2H), 4.08-3.87 (m, 2H), 3.65-3.59 (m, 1H), 2.21-2.11 (m, 2H), 1.98 (s, 3H), 1.91-1.75 (m, 2H), 1.37 (s, 9H).

Mass m/z: 435.0 [M⁺+1].

Synthesis of (S)-1-((S)-3-acetoxy-2-(benzyloxycarbonylamino)-propanoyl)-pyrrolidine-2-carboxylic acid (3)

To a solution of compound 2 (1 g, 2.30 mmol) in CH₂Cl₂ (5 mL) was added 20% TFA-DCM (10 mL) and stirred at RT for 2 h. The reaction mixture was diluted with water (10 mL) and extracted with EtOAc (2×15 mL). The organic layer was dried over anhydrous Na₂SO₄ and concentrated under reduced pressure to yield compound 3 (800 mg, 92%).

¹H-NMR: (200 MHz, DMSO-d₆): δ 12.58 (br s, 1H), 7.81-7.77 (d, J=8.0 Hz, 1H), 7.35-7.27 (m, 5H), 5.04-4.96 (m, 2H), 4.66-4.60 (m, 1H), 4.32-4.24 (m, 2H), 4.04-3.86 (m, 1H), 3.66-3.59 (t, J=12.6 Hz, 2H), 2.17-2.07 (m, 3H), 1.98-1.80 (m, 4H).

Mass m/z: 379.0 [M⁺+1].

Synthesis of (2S,3R)-methyl 2-((S)-1-((S)-1-((R)-3-acetoxy-2-(benzyloxycarbonylamino)-propanoyl)-pyrrolidine-2-carbonyl)pyrrolidine-2-carboxamido)-3-hydroxybutanoate (5)

Compound 3 (1.0 g, 2.64 mmol) was dissolved in CH₂Cl₂ (10 mL), NMM (0.32 g, 3.17 mmol) and IBCF (0.41 g, 3.04 mmol) were added to the reaction mixture at −15° C. and stirred for minutes under inert atmosphere. A mixture of (2S,3R)-methyl 3-hydroxy-2-((S)-pyrrolidine-2-carboxamido)-butanoate (4) (0.73 g, 3.17 mmol) and NMM (0.35 mL) in DMF (3 mL) were added drop wise to the reaction mixture at −15° C. and stirring was continued for another 3 h at RT. The reaction mixture was diluted with DCM (200 mL), washed with water (20 mL), citric acid solution (2×20 mL) and brine (2×50 mL). The separated organic layer was dried over anhydrous $Na_2SO_4$ and concentrated under reduced pressure. The crude residue obtained was purified by silica gel column chromatography eluting with 5% $CH_3OH$/EtOAc to afford compound (5) (0.29 g, 19%).

$^1$H-NMR: (500 MHz, DMSO-$d_6$): δ 7.83-7.81 (m, 1H), 7.72-7.70 (m, 1H), 7.36-7.35 (m, 5H), 5.07-5.01 (m, 2H), 4.99-4.93 (m, 1H), 4.58 (s, 1H), 4.50-4.48 (m, 1H), 4.26-4.22 (m, 2H), 4.07-4.00 (m, 2H), 3.89-3.86 (m, 1H), 3.61-3.55 (m, 5H), 3.53 (s, 1H), 3.39 (s, 1H), 2.12 (s, 1H), 1.98 (s, 3H), 1.94-1.83 (m, 4H), 1.81-1.80 (m, 3H), 1.05 (d, J=6.5 Hz, 3H).

Mass m/z: 591.0 [M$^+$+1].

Synthesis of benzyl-(R)-1-((S)-2-((S)-2-((2S,3R)-1-(aminooxy)-3-hydroxy-1-oxobutan-2-ylcarbamoyl)-pyrrolidine-1-carbonyl)-pyrrolidin-1-yl)-3-hydroxy-1-oxopropan-2-ylcarbamate (6)

A solution of methanolic ammonia (3 mL) was added to compound 5 (0.28 g, 0.47 mmol) and stirred at RT for 18 h. The volatiles were evaporated under reduced pressure to afford compound 6 (0.21 g, 82.3%).

$^1$H-NMR: (500 MHz, DMSO-$d_6$): δ 7.38-7.31 (m, 5H), 7.26 (s, 1H), 7.10-7.03 (m, 2H), 6.65 (br s, 1H), 5.04-5.01 (m, 2H), 4.98-4.84 (m, 1H), 4.76-4.75 (m, 1H), 4.61 (s, 1H), 4.38-4.31 (m, 2H), 4.02-4.00 (m, 2H), 3.77-3.74 (m, 1H), 3.67-3.56 (m, 3H), 3.44-3.37 (m, 2H), 2.14-1.86 (m, 8H), 1.01-1.00 (m, 3H).

Mass m/z: 550 [M$^+$+1].

Synthesis of (S)—N-((2S,3R)-1-amino-3-hydroxy-1-oxobutan-2-yl)-1-((S)-1-((S)-2-amino-3-hydroxypropanoyl)-pyrrolidine-2-carbonyl)-pyrrolidine-2-carboxamide (Compound A)

To a solution of compound 6 (0.21 g, 0.39 mmol) in methanol (5 mL) was added 10% Pd/C (30 mg) and the reaction mixture was stirred under hydrogen atmosphere for 2 h. The reaction mixture was filtered over celite, solvent was evaporated in vacuo, and the crude residue obtained was triturated with diethyl ether to yield A (130 mg, 83.3%).

$^1$H-NMR: (500 MHz, DMSO-$d_6$) (Rotamers): δ 7.39 (d, J=8.0 Hz, 1H), 7.08-7.03 (m, 2H), 6.65 (br s, 1H), 4.89-4.85 (m, 1H), 1.61-1.59 (m, 1H), 4.39-4.38 (m, 1H), 4.02-4.00 (m, 2H), 3.68-3.52 (m, 4H), 3.43-3.36 (m, 2H), 3.22-3.10 (m, 2H), 2.19-2.13 (m, 1H), 2.07-1.98 (m, 1H), 1.93-1.81 (m, 5H), 1.75 (s, 2H), 1.01-1.00 (m, 3H).

LCMS m/z: 400.2 [M$^+$+1].

HPLC Purity: 99.27%.

Synthesis of (S)-1-(benzyloxycarbonyl)pyrrolidine-2-carboxylic acid (8)

To a stirred solution of (S)-pyrrolidine-2-carboxylic acid (7) (2.0 g, 17.39 mmol) in THF:$H_2O$ (20 mL, 1:1) were added $Na_2CO_3$ (2.76 g, 26.08 mmol) and Cbz-Cl (3.54 g, 20.80 mmol) and stirred at RT for 18 h. The reaction mixture was washed with EtOAc (10 mL) and the aqueous layer was acidified with 3N HCl and extracted with EtOAc (2×20 mL). The combined organic layer was washed with brine, dried over anhydrous $Na_2SO_4$ and concentrated under reduced pressure to yield compound 8 (3.0 g, 69.7%).

$^1$H-NMR: (500 MHz, DMSO-$d_6$): δ 12.62 (br s, 1H), 7.36-7.22 (m, 5H), 5.12-5.00 (m, 2H), 4.24-4.15 (dd, J=5.0, 36.0 Hz, 1H), 3.46-3.31 (m, 2H), 2.25-2.15 (m, 1H), 1.94-1.79 (m, 3H).

Mass m/z: 250.0 [M$^+$+1].

Synthesis of (S)-benzyl 2-((2S,3R)-3-hydroxy-1-methoxy-1-oxobutan-2-ylcarbamoyl)pyrrolidine-1-carboxylate (9)

Compound 8 (5.0 g, 20.08 mmol) was dissolved in $CH_2Cl_2$ (50 mL), NMM (2.43 mL, 22.08 mmol) and IBCF (2.74 mL, 23.09 mmol) were added and stirred at −15° C. for 30 minutes under inert atmosphere. A mixture of (2S,3R)-methyl 2-amino-3-hydroxybutanoate (2.93 g, 22.08 mmol) and NMM (2.43 mL, 22.08 mmol) in DMF (15 mL) were added drop wise at −15° C. The resultant reaction mixture was stirred at RT for 3 h. It was diluted with DCM (200 mL) and the organic layer was washed with water (50 mL), brine (50 mL), dried over anhydrous $Na_2SO_4$ and concentrated under reduced pressure. The obtained crude was purified by silica gel column chromatography eluting with 30% EtOAc/Hexane to afford compound 9 (3.1 g, 42%).

$^1$H-NMR: (500 MHz, DMSO-$d_6$) (Rotamers): δ 7.98-7.94 (m, 1H), 7.35-7.27 (m, 5H), 5.09-4.94 (m, 3H), 4.44 (dd, J=5.5, 8.5 Hz, 1H), 4.29-4.27 (m, 1H), 4.12 (s, 1H), 3.62 (s, 3H), 3.44-3.30 (m, 2H), 2.20-2.08 (m, 1H), 1.87-1.78 (m, 3H), 1.08-0.94 (2d, 3H).

Mass m/z: 365.0 [M$^+$+1].

Example 2

Synthesis of (S)—N—((S)-1-amino-3-hydroxy-1-oxopropan-2-yl)-1-((S)-1-((2S,3R)-2-amino-3-hydroxybutanoyl)pyrrolidine-2-carbonyl)pyrrolidine-2-carboxamide (Compound B)

The following reaction sequence was used (Scheme B) to synthesize (S)—N—((S)-1-amino-3-hydroxy-1-oxopropan-2-yl)-1-((S)-1-((2S,3R)-2-amino-3-hydroxybutanoyl)pyrrolidine-2-carbonyl)pyrrolidine-2-carboxamide:

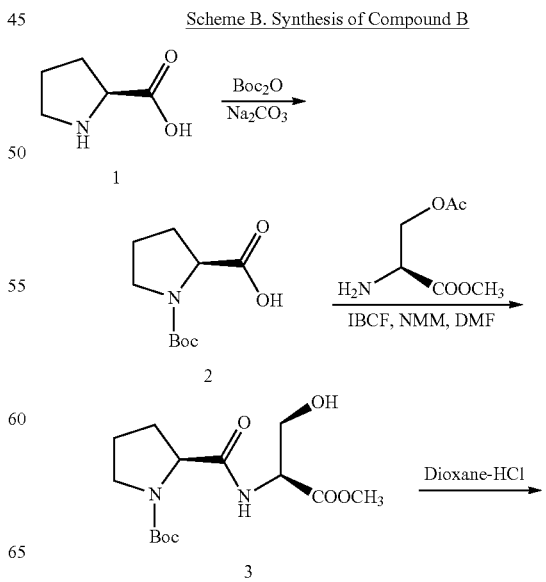

Scheme B. Synthesis of Compound B

-continued

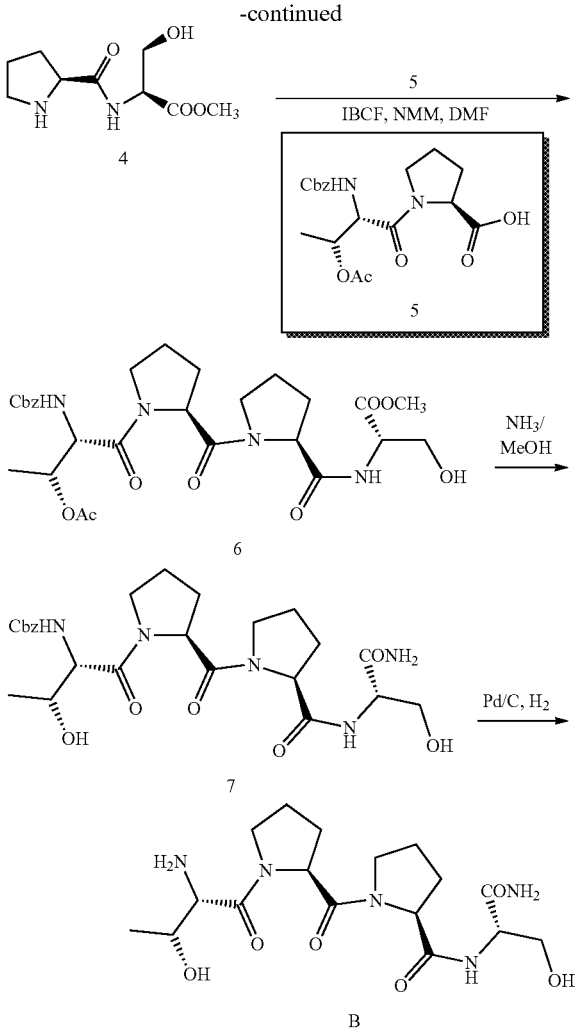

Synthesis of (S)-1-(tert-butoxycarbonyl)-pyrrolidine-2-carboxylic acid (2)

To an ice cold stirred solution of (S)-pyrrolidine-2-carboxylic acid (1) (3.0 g, 26.08 mmol) in THF:H$_2$O (60 mL, 1:1) were added Na$_2$CO$_3$ (5.52 g, 52.16 mmol), Boc$_2$O (6.25 g, 26.69 mmol) and stirred at RT for 16 h. The reaction mixture was diluted with water and washed with EtOAc (50 mL). The aqueous layer was acidified with 2N HCl and extracted with EtOAc (2×100 mL). The combined organic layer was dried over anhydrous Na$_2$SO$_4$ and concentrated under reduced pressure to yield the (S)-1-(tert-butoxycarbonyl)-pyrrolidine-2-carboxylic acid (2) (4.8 g, 86%).

$^1$H-NMR: (500 MHz, DMSO-d$_6$): δ 12.49 (br s, 1H), 4.08-4.03 (m, 1H), 3.36-3.24 (m, 2H), 2.22-2.11 (m, 1H), 1.87-1.76 (m, 3H), 1.39 (s, 9H).

Mass m/z: 216.0 [M$^+$+1].

Synthesis of (S)-tert-butyl 2-((S)-3-hydroxy-1-methoxy-1-oxopropan-2-ylcarbamoyl)-pyrrolidine-1-carboxylate (3)

Compound 2 (2.0 g, 9.00 mmol) was dissolved in CH$_2$Cl$_2$ (10 mL) cooled to −15° C., NMM (1.12 mL, 10.2 mmol) and IBCF (1.26 mL, 1.15 mmol) were added and stirred at 0° C. for 20 minutes. A mixture of (S)-methyl 2-amino-3-hydroxypropanoate (1.59 g, 10.2 mmol) and NMM (1.12 mL) in DMF (3 mL) were added drop wise at −15° C. and the resultant reaction mixture was stirred at RT for 1 h. It was diluted with DCM (200 mL), water (50 mL) and washed with 2N HCl (20 mL) and brine (2×50 mL). The separated organic layer was dried over anhydrous Na$_2$SO$_4$ and concentrated under reduced pressure. The crude residue obtained was purified by silica gel column chromatography eluting with 20% EtOAc/Hexane to afford compound 3 (2.3 g) as a syrup.

Mass m/z: 317.0 [M$^+$+1].

Synthesis of (S)-methyl 3-hydroxy-2-((S)-pyrrolidine-2-carboxamido)propionate (4)

(S)-Tert-butyl-2-((S)-3-hydroxy-1-methoxy-1-oxopropan-2-ylcarbamoyl)-pyrrolidine-1-carboxylate (3) (500 mg, 1.58 mmol) was dissolved in 1,4-dioxane (3 mL) and a HCl solution in dioxane (3.16 mL, 3.16 mmol) was added stirred at RT for 4 h. The volatiles were evaporated under reduced pressure to afford compound 4 (280 mg) as solid.

$^1$H-NMR: (200 MHz, DMSO-d$_6$): δ 9.99 (br s, 1H), 9.12-9.08 (m, 1H), 8.53 (br s, 1H), 5.48 (br s, 2H), 4.43-4.22 (m, 2H), 3.82-3.67 (m, 4H), 3.56 (s, 3H), 2.36-2.27 (m, 1H), 1.93-1.86 (m, 3H).

Mass m/z: 217.0 [M$^+$+1].

Synthesis of (S)-methyl 2-((S)-1-((S)-1-((2R,3S)-3-acetoxy-2-(benzyloxycarbonylamino)-butanoyl)-pyrrolidine-2-carbonyl)-pyrrolidine-2-carboxamido)-3-hydroxypropanoate (6)

(2S)-1-((2R)-3-acetoxy-2-(benzyloxycarbonylamino)-butanoyl)-pyrrolidine-2-carboxylic acid (5) (1.3 g, 2.62 mmol) was dissolved in CH$_2$Cl$_2$ (15 mL), NMM (0.43 mL) and IBCF (0.51 mL) was added at −10° C. and stirred for 30 minutes under inert atmosphere. A mixture of (S)-methyl-3-hydroxy-2-((S)-pyrrolidine-2-carboxamido)-propionate (4) (992 mg, 3.93 mmol) and NMM (0.43 mL) in DMF (5 mL) were added drop wise to the reaction mixture and stirring was continued for another 3 h at RT. The reaction mixture was diluted with DCM (200 mL), washed with water (20 mL), citric acid solution (2×20 mL) and brine (2×50 mL). The separated organic layer was dried over anhydrous Na$_2$SO$_4$ and concentrated under reduced pressure. The obtained crude material was purified by silica gel column chromatography eluting with 5% CH$_3$OH/CH$_2$Cl$_2$ to afford compound 6 (270 mg, 17.5%).

$^1$H-NMR: (500 MHz, DMSO-d$_6$): δ 8.13 (d, J=8.0 Hz, 1H), 7.74 (d, J=7.5 Hz, 1H), 7.38-7.31 (m, 5H), 5.08-4.96 (m, 3H), 4.85-4.82 (m, 1H), 4.56 (d, J=8.0 Hz, 1H), 4.44-4.42 (m, 2H), 4.27 (d, J=7.0 Hz, 1H), 4.10 (d, J=10.5 Hz, 2H), 3.81-3.78 (m, 1H), 3.72-3.70 (m, 1H), 3.61-3.59 (m, 3H), 3.54-3.50 (m, 2H), 2.16-2.14 (m, 1H), 2.05-2.01 (m, 1H), 1.90 (s, 3H), 1.87-1.86 (m, 3H), 1.85-1.84 (m, 3H), 1.21-1.20 (d, J=6.0 Hz, 3H).

Mass m/z: 591.0 [M$^+$+1].

Synthesis of Benzyl-(2R,3S)-1-((S)-2-((S)-2-((S)-1-(aminooxy)-3-hydroxy-1-oxopropan-2-ylcarbamoyl) pyrrolidine-1-carbonyl)pyrrolidin-1-yl)-3-hydroxy-1-oxobutan-2-ylcarbamate (7)

To a solution of compound 6 (250 g, 0.42 mmol) in CH$_3$OH (2 mL) was added MeOH—NH$_3$ (10 mL) and was stirred at RT for 16 h. The volatiles were evaporated under reduced pressure to afford compound 7 (190 mg, 84%).

¹H-NMR: (500 MHz, DMSO-d₆): δ 7.60 (d, J=7.5 Hz, 1H), 7.35-7.30 (m, 5H), 7.18 (d, J=7.0 Hz, 1H), 7.11-7.06 (m, 2H), 5.05-4.97 (m, 2H), 4.82-4.81 (m, 1H), 4.60-4.59 (m, 2H), 4.33-4.31 (m, 1H), 4.15-4.08 (m, 2H), 3.81-3.79 (m, 1H), 3.72-3.64 (m, 2H), 3.59-3.53 (m, 4H), 2.14 (s, 1H), 2.03 (d, J=9.0 Hz, 1H), 1.95-1.85 (m, 5H), 1.75 (s, 1H), 1.10 (d, J=6.5 Hz, 3H).

Mass m/z: 550.0 [M⁺+1].

Synthesis of (S)—N—((S)-1-amino-3-hydroxy-1-oxopropan-2-yl)-1-((S)-1-((2S,3R)-2-amino-3-hydroxybutanoyl)pyrrolidine-2-carbonyl)-pyrrolidine-2-carboxamide (B)

To a solution of compound 7 (190 mg, 0.35 mmol) in methanol (5 mL) was added 10% Pd/C (50 mg) and the reaction mixture was stirred under hydrogen atmosphere for 2 h. The reaction mixture was filtered through a celite pad, solvent was evaporated in vacuo and the crude was purified by column chromatography on basic alumina using 0-5% CH₃OH in CH₂Cl₂ as eluent to yield compound B (130 mg, 73%).

¹H-NMR: (500 MHz, DMSO-d₆): δ 7.65-7.60 (m, 1H), 7.12-7.03 (m, 2H), 4.81 (br s, 1H), 4.58-4.57 (m, 1H), 4.49 (m, 1H), 4.38-4.19 (m, 1H), 4.10-4.06 (m, 1H), 3.69-3.62 (m, 2H), 3.59-3.56 (m, 4H), 3.49-3.45 (m, 2H), 3.37-3.26 (m, 2H), 2.19-2.15 (m, 1H), 2.09-1.99 (m, 1H), 1.95-1.84 (m, 5H), 1.75 (s, 1H), 1.06 (d, J=13.0 Hz, 3H).

LCMS m/z: 400.8 [M⁺+1].

HPLC Purity: 97.71%.

Example 3

Synthesis of (S)—N—((S)-1-amino-3-hydroxy-1-oxopropan-2-yl)-1-((S)-1-((S)-2-amino-3-hydroxy-propanoyl)-pyrrolidine-2-carbonyl)-pyrrolidine-2-carboxamide (Compound C)

The following reaction sequence was used (Scheme C) to synthesize (S)—N—((S)-1-amino-3-hydroxy-1-oxopropan-2-yl)-1-((S)-1-((S)-2-amino-3-hydroxy-propanoyl)-pyrrolidine-2-carbonyl)-pyrrolidine-2-carboxamide

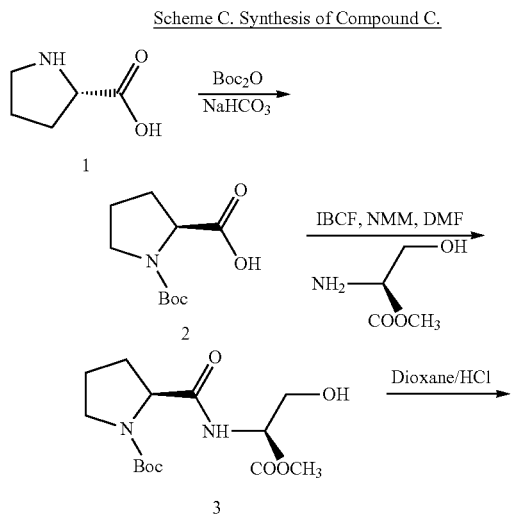

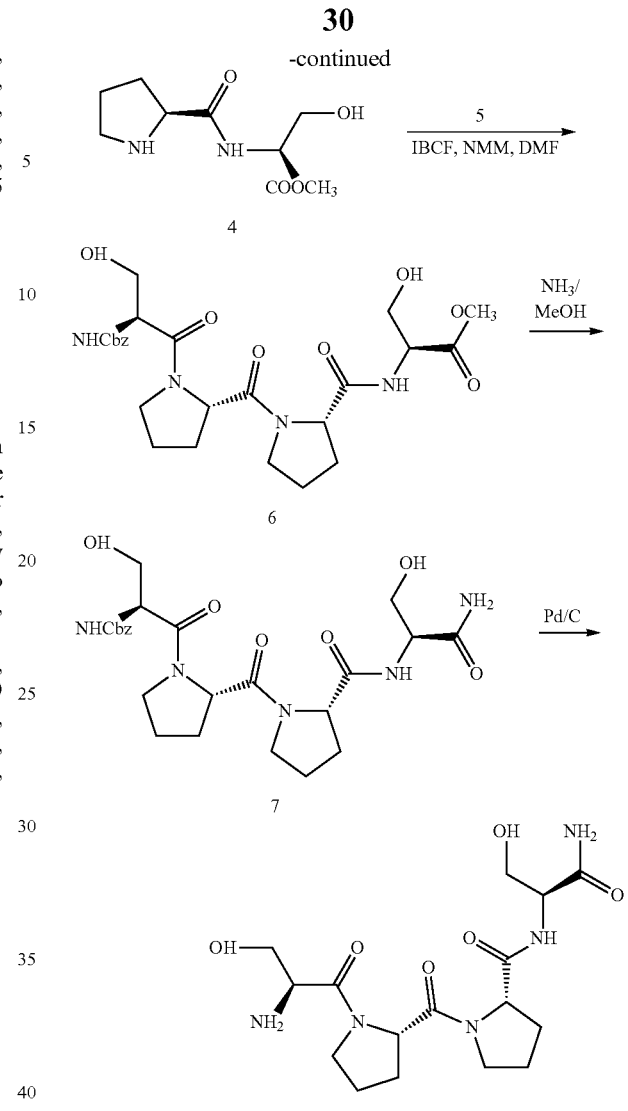

Synthesis of (S)-1-(tert-butoxycarbonyl)-pyrrolidine-2-carboxylic acid (2)

To a stirred solution of (S)-pyrrolidine-2-carboxylic acid (3.0 g, 26.08 mmol) in THF:H₂O (60 mL, 1:1) at 0° C. were added Na₂CO₃ (5.52 g, 52.16 mmol) and Boc₂O (6.25 g, 26.69 mmol) and stirred at RT for 16 h. The reaction mixture was diluted with water and washed with EtOAc (50 mL). The aqueous layer was acidified with 2N HCl and extracted with EtOAc (2×50 mL). The combined organic layer was dried over anhydrous Na₂SO₄ and concentrated under reduced pressure to yield the (S)-1-(tert-butoxycarbonyl)-pyrrolidine-2-carboxylic acid 2 (4.8 g, 85.7%).

¹H-NMR: (500 MHz, DMSO-d₆): δ 12.49 (br s, 1H), 4.08-4.03 (m, 1H), 3.36-3.24 (m, 2H), 2.22-2.11 (m, 1H), 1.87-1.76 (m, 3H), 1.39 (s, 9H).

Mass m/z: 216.0 [M⁺+1].

Synthesis of (S)-tert-butyl 2-((S)-3-hydroxy-1-methoxy-1-oxopropan-2-ylcarbamoyl)pyrrolidine-1-carboxylate (3)

Compound 2 (2.0 g, 9.00 mmol) was dissolved in CH₂Cl₂ (10 mL) cooled to −15° C., NMM (1.12 mL, 10.2 mmol) and IBCF (1.26 mL, 1.15 mmol) were added and stirred at 0° C. for 20 minutes. A mixture of (S)-methyl-2-amino-3-hydroxypropanoate (1.59 g, 10.2 mmol) and NMM (1.12 mL) in DMF (3 mL) were added drop wise at −15° C. The resultant reaction mixture was stirred at RT for 1 h. The reaction mixture was diluted with DCM (200 mL) and water (25 mL) and was washed with 2N HCl (20 mL) and brine (10 mL). The separated organic layer was dried over anhydrous $Na_2SO_4$ and concentrated under reduced pressure. The obtained crude material was purified by silica gel column chromatography eluting with 20% EtOAc/Hexane to afford compound 3 (2.3 g) as solid.

Mass m/z: 317.0 [M$^+$+1].

Synthesis of (S)-methyl 3-hydroxy-2-((S)-pyrrolidine-2-carboxamido) propanoate (4)

To a solution of (S)-tert-butyl-2-((S)-3-hydroxy-1-methoxy-1-oxopropan-2-ylcarbamoyl)pyrrolidine-1-carboxylate 3 (500 mg, 1.58 mmol) in 1,4-dioxane (3 mL) was added a solution of HCl in dioxane (3.16 mL, 3.16 mmol) and stirred at RT for 4 h. The volatiles were evaporated under reduced pressure to afford compound 4 (280 mg) as solid.

$^1$H-NMR: (200 MHz, DMSO-$d_6$): δ 9.99 (br s, 1H), 9.12-9.08 (m, 1H), 8.53 (br s, 1H), 5.48 (br s, 2H), 4.43-4.22 (m, 2H), 3.82-3.67 (m, 4H), 3.56 (s, 3H), 2.36-2.27 (m, 1H), 1.93-1.86 (m, 3H).

Mass m/z: 217.0 [M$^+$+1].

Synthesis of (S)-methyl 2-((S)-1-((S)-1-((S)-2-(benzyloxycarbonylamino)-3-hydroxypropanoyl)-pyrrolidine-2-carbonyl)-pyrrolidine-2-carboxamido)-3-hydroxypropanoate (6)

(S)-1-((S)-3-Acetoxy-2-(benzyloxycarbonylamino)-propanoyl)-pyrrolidine-2-carboxylic acid (5) (400 mg, 1.05 mmol) was dissolved in $CH_2Cl_2$ (2 mL), NMM (0.13 mL) and IBCF (0.14 mL) were added at −15° C. and stirred for 30 minutes under inert atmosphere. A mixture of (S)-methyl-3-hydroxy-2-((S)-pyrrolidine-2-carboxamido)-propanoate hydrochloride (4) (293 mg, 1.16 mmol) and NMM (0.13 mL) in DMF (2 mL) were added drop wise to the reaction mixture and stirring was continued for another 3 h at RT. The reaction mixture was diluted with DCM (200 mL), washed with water (20 mL) and brine (10 mL). The separated organic layer was dried over anhydrous $Na_2SO_4$ and concentrated under reduced pressure. The obtained crude material was purified by silica gel column chromatography eluting with 5% $CH_3OH/CH_2Cl_2$ to afford compound 6 (80 mg, 13%).

$^1$H-NMR: (500 MHz, DMSO-$d_6$): δ 8.09 (d, J=7.5 Hz, 1H), 7.71 (d, J=8.0 Hz, 1H), 7.36-7.31 (m, 6H), 5.07-4.99 (m, 3H), 4.59-4.58 (m, 2H), 4.41-4.40 (m, 1H), 4.29-4.24 (m, 3H), 3.86 (t, J=9.5 Hz, 1H), 3.72-3.68 (m, 1H), 3.64-3.57 (m, 3H), 3.40-3.38 (m, 3H), 2.14-2.01 (m, 2H), 1.98 (s, 3H), 1.90-1.80 (m, 6H).

Mass m/z: 535.0 [M$^+$+1].

Synthesis of Benzyl-(S)-1-((S)-2-((S)-2-((S)-1-amino-3-hydroxy-1-oxopropan-2-ylcarbamoyl)pyrrolidine-1-carbonyl)pyrrolidin-1-yl)-3-hydroxy-1-oxopropan-2-ylcarbamate (7)

To a solution of (S)-methyl-2-((S)-1-((S)-1-((S)-2-(benzyloxycarbonylamino)-3-hydroxypropanoyl)-pyrrolidine-2-carbonyl)-pyrrolidine-2-carboxamido)-3-hydroxypropanoate (6) (60 mg, 1.04 mmol) in MeOH was added MeOH—$NH_3$ (3 mL) was stirred at RT for 16 h. The volatiles were evaporated under reduced pressure to afford compound 7 (30 mg, 55%).

$^1$H-NMR: (500 MHz, DMSO-$d_6$): δ 7.60 (d, J=7.5 Hz, 1H), 7.36-7.31 (m, 6H), 7.11-7.06 (m, 2H), 5.04-4.98 (m, 2H), 4.82-4.74 (m, 2H), 4.61-4.59 (m, 1H), 4.36-4.30 (m, 2H), 4.10-4.07 (m, 1H), 3.67-3.65 (m, 2H), 3.59-3.55 (m, 6H), 3.44-3.40 (m, 2H), 1.95-1.92 (m, 6H).

Mass m/z: 520.0 [M$^+$+1].

Synthesis of (S)—N—((S)-1-amino-3-hydroxy-1-oxopropan-2-yl)-1-((S)-1-((S)-2-amino-3-hydroxypropanoyl)-pyrrolidine-2-carbonyl)-pyrrolidine-2-carboxamide (C)

Benzyl-(S)-1-((S)-2-((S)-2-((S)-1-amino-3-hydroxy-1-oxopropan-2-ylcarbamoyl)pyrrolidine-1-carbonyl)pyrrolidin-1-yl)-3-hydroxy-1-oxopropan-2-ylcarbamate 7 (300 mg, 0.57 mmol) was dissolved in methanol (8 mL), 10% Pd/C (50 mg) was added and reaction mixture was stirred under hydrogen atmosphere for 2 h. The reaction mixture was filtered and the filtrate was concentrated under reduced pressure to yield compound C (150 mg, 68%).

$^1$H-NMR: (500 MHz, DMSO-$d_6$) (Rotamers): δ 7.62 (d, J=8.0 Hz, 1H), 7.24 (br s, 1H), 7.14-7.07 (m, 2H), 4.87-4.82 (m, 2H), 4.59-4.57 (m, 1H), 4.37-4.31 (m, 2H), 4.11-4.07 (m, 2H), 3.70-3.39 (m, 8H), 2.17-2.01 (m, 2H), 1.95-1.79 (m, 6H).

LCMS m/z: 386.4 [M$^+$+1].
HPLC Purity: 98.45%.

Example 4

Synthesis of N-((2S,3R)-1-amino-3-hydroxy-1-oxobutan-2-yl)-1-((S)-1-((2S,3R)-2-amino-3-hydroxybutanoyl)-pyrrolidine-2-carbonyl)-2-benzylpyrrolidine-2-carboxamide (Compound D & E)

The following reaction sequence was used (Scheme D) to synthesize N-((2S,3R)-1-amino-3-hydroxy-1-oxobutan-2-yl)-1-((S)-1-((2S,3R)-2-amino-3-hydroxybutanoyl)-pyrrolidine-2-carbonyl)-2-benzsaylpyrrolidine-2-carboxamide (Compound D & E):

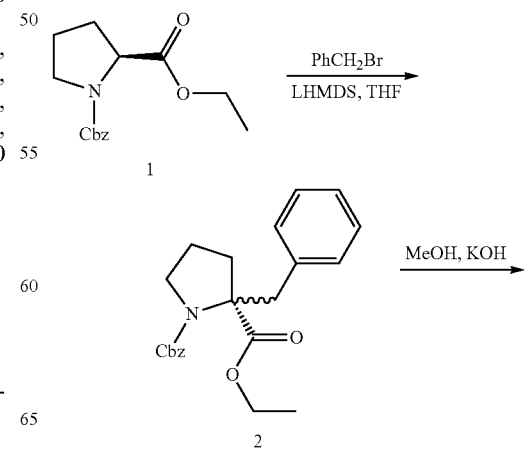

Scheme D. Synthesis of Compound D & E.

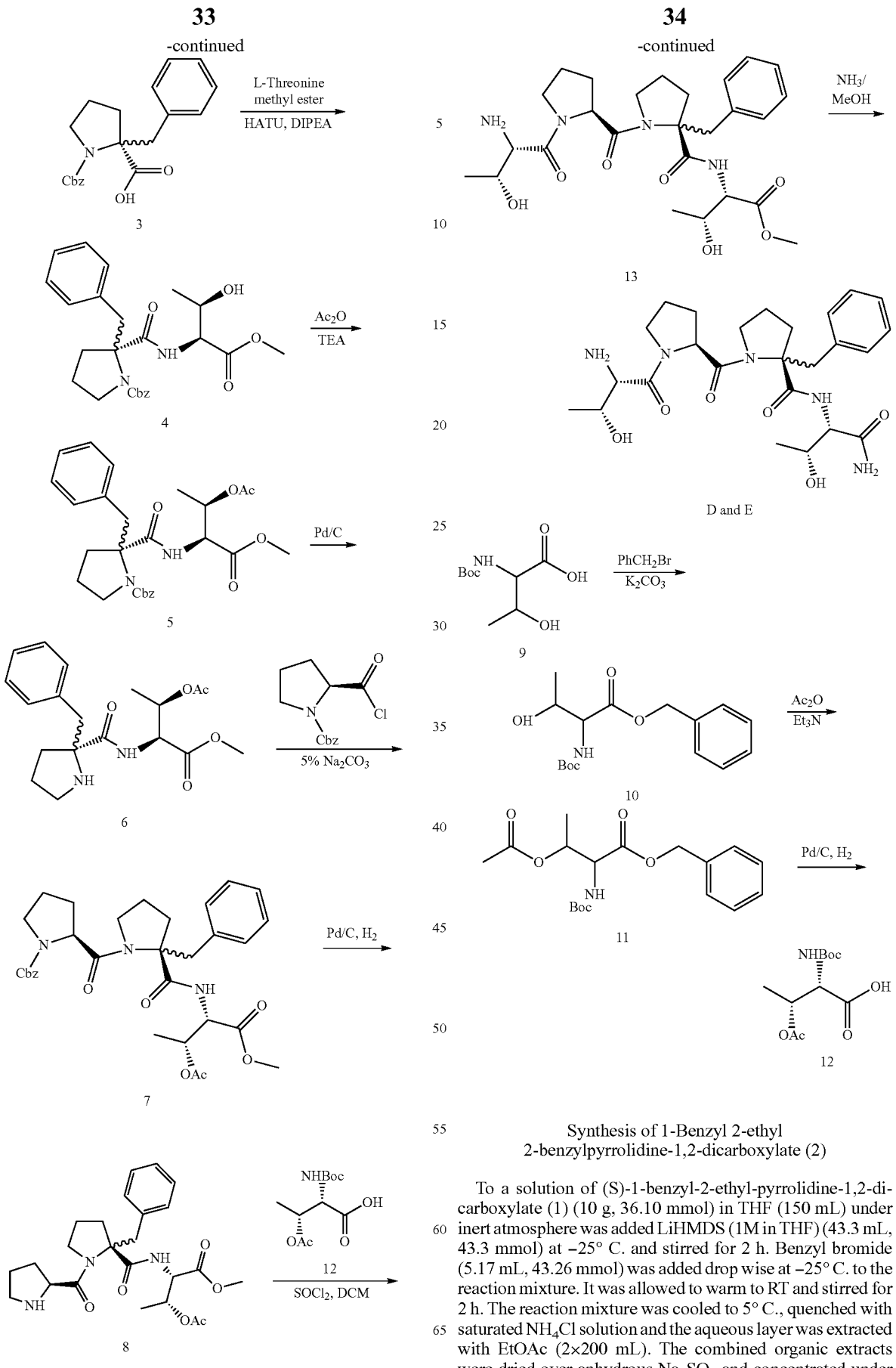

Synthesis of 1-Benzyl 2-ethyl 2-benzylpyrrolidine-1,2-dicarboxylate (2)

To a solution of (S)-1-benzyl-2-ethyl-pyrrolidine-1,2-dicarboxylate (1) (10 g, 36.10 mmol) in THF (150 mL) under inert atmosphere was added LiHMDS (1M in THF) (43.3 mL, 43.3 mmol) at −25° C. and stirred for 2 h. Benzyl bromide (5.17 mL, 43.26 mmol) was added drop wise at −25° C. to the reaction mixture. It was allowed to warm to RT and stirred for 2 h. The reaction mixture was cooled to 5° C., quenched with saturated NH$_4$Cl solution and the aqueous layer was extracted with EtOAc (2×200 mL). The combined organic extracts were dried over anhydrous Na$_2$SO$_4$ and concentrated under reduced pressure. The crude residue obtained was purified by silica gel column chromatography eluting with 5% EtOAc/hexane to afford compound 2 (13 g, 75%) as liquid.

$^1$H-NMR: (200 MHz, DMSO-d$_6$): δ 7.47-7.32 (m, 5H), 7.27-7.16 (m, 3H), 7.07-7.04 (m, 2H), 5.29-5.06 (m, 2H), 4.16-3.89 (m, 2H), 3.57-3.33 (m, 2H), 3.02-2.78 (m, 2H), 2.13-1.89 (m, 2H), 1.56-1.51 (m, 1H), 1.21-1.04 (m, 3H), 0.93-0.79 (m, 1H).

Mass m/z: 368.2 [M$^+$+1].

Synthesis of 2-benzyl-1-(benzyloxycarbonyl)-pyrrolidine-2-carboxylic acid (3)

To a stirred solution of compound 2 (8.0 g, 21.79 mmol) in CH$_3$OH (20 mL) was added 2N aqueous KOH (20 mL) and heated up to 100° C. and stirred for 16 h. The volatiles were evaporated under reduced pressure. The residue obtained was diluted with ice cold water (50 mL) and washed with ether (50 mL). The aqueous layer was acidified to pH~2 using HCl solution and extracted with EtOAc (2×100 mL). The combined organic layer was dried over anhydrous Na$_2$SO$_4$ and concentrated under reduced pressure to afford compound 3 (6 g, 81%) as an off white solid.

$^1$H-NMR: (200 MHz, DMSO-d$_6$): δ 12.71 (br s, 1H), 7.40-7.30 (m, 5H), 7.25-7.19 (m, 3H), 7.07-7.00 (m, 2H), 5.27-5.02 (m, 2H), 3.59-3.32 (m, 2H), 3.02-2.83 (m, 2H), 2.13-1.91 (m, 2H), 1.58-1.49 (m, 1H), 0.90-0.77 (m, 1H).

Mass m/z: 340.1 [M$^+$+1].

Synthesis of Benzyl-2-benzyl-2-((2S,3R)-3-hydroxy-1-methoxy-1-oxobutan-2-ylcarbamoyl)-pyrrolidine-1-carboxylate (4)

To a suspension of compound 3 (1.0 g, 2.94 mmol), L-threonine methyl ester (471 mg, 3.53 mmol) in DMF (20 mL) was added HATU (1.12 g, 2.94 mmol) and DIPEA (1.58 mL, 8.84 mmol) at 5° C. The reaction mixture was stirred at RT for 16 h. It was diluted with EtOAc (150 mL) and washed with water (2×30 mL). The organic layer was washed with brine, dried over Na$_2$SO$_4$, concentrated and purified by silica gel column chromatography 50% EtOAc/Hexane as eluent to yield compound 4 (1.0 g, 74%).

$^1$H-NMR: (200 MHz, DMSO-d$_6$): δ 7.62-7.59 (m, 1H), 7.44-7.31 (m, 5H), 7.21-7.18 (m, 3H), 7.06-6.99 (m, 2H), 5.25-5.24 (m, 1H), 5.12-4.94 (m, 2H), 4.30 (s, 1H), 4.15-4.08 (m, 1H), 3.66-3.64 (m, 3H), 3.63-3.49 (m, 2H), 3.14 (s, 1H), 2.89 (s, 1H), 2.09-2.02 (m, 2H), 1.56-1.51 (m, 1H), 1.09-0.98 (m, 4H).

Mass m/z: 455.1 [M$^+$+1], 477.3 [M+Na].

Synthesis of Benzyl-2-((2S,3R)-3-acetoxy-1-methoxy-1-oxobutan-2-ylcarbamoyl)-2-benzylpyrrolidine-1-carboxylate (5)

Compound 4 (3 g, 6.60 mmol) was dissolved in THF (30 mL), Et$_3$N (1.11 mL, 7.92 mmol) and Ac$_2$O (742 mg, 7.26 mmol) were added at RT. The reaction mixture was stirred at RT for 2 h. The volatiles were evaporated under reduced pressure and the residue obtained was diluted with CH$_2$Cl$_2$ and washed with dilute HCl. The combined organic extracts were dried over Na$_2$SO$_4$ and concentrated under reduced pressure. The crude residue was purified by column chromatography using 30% EtOAc/Hexane as eluent to yield compound 5 (2.5 g, 76%).

$^1$H-NMR: (500 MHz, DMSO-d$_6$) (Rotamers): δ 8.15-7.71 (m, 1H), 7.42-7.04 (m, 10H), 5.30-5.19 (m, 2H), 5.11-5.09 (m, 1H), 4.99-4.93 (m, 1H), 4.67-4.62 (m, 1H), 3.66-3.64 (m, 3H), 3.55-3.46 (m, 2H), 3.38-3.35 (m, 1H), 2.88-2.69 (m, 1H), 2.17-2.00 (m, 2H), 1.98-1.92 (m, 3H), 1.56-1.46 (m, 1H), 1.23-1.17 (m, 3H), 1.02-0.86 (m, 1H).

LCMS m/z: 497.4 [M$^+$+1].

Synthesis of (2S,3R)-methyl 3-acetoxy-2-(2-benzylpyrrolidine-2-carboxamido)-butanoate (6)

To a stirring solution of compound 5 (4 g, 8.06 mmol) in ethanol (50 mL) was added 10% Pd/C (1.2 g) and the reaction mixture was stirred under H$_2$ atmosphere (balloon pressure) for 4 h. It was filtered through celite pad and the filtrate was concentrated under reduced pressure to yield compound 6 (2.2 g, 75%).

$^1$H-NMR: (500 MHz, DMSO-d$_6$) (Rotamers): δ 8.22-8.17 (m, 1H), 7.24-7.16 (m, 5H), 5.17 (t, J=11.5 Hz, 1H), 4.48-4.42 (m, 1H), 3.60-3.54 (s, 3H), 3.20 (t, J=13.5 Hz, 1H), 3.06-2.97 (m, 1H), 2.82-2.68 (m, 3H), 2.08-2.02 (m, 1H), 1.89 (s, 3H), 1.72-1.51 (m, 3H), 1.10 (2d, 3H).

LCMS m/z: 363 [M$^+$+1], 385 [M+Na].

Synthesis of (S)-benzyl 2-(2-((2S,3R)-3-acetoxy-1-methoxy-1-oxobutan-2-ylcarbamoyl)-2-benzylpyrrolidine-1-carbonyl)pyrrolidine-1-carboxylate (7)

To a stirred solution of compound 6 (1 g, 2.76 mmol) and Na$_2$CO$_3$ (732 mg, 6.90 mmol) in CH$_2$Cl$_2$:H$_2$O (20 mL, 1:1) was added a solution of acid chloride [To a solution of (S)-1-(benzyloxycarbonyl)pyrrolidine-2-carboxylic acid (825 mg, 3.31 mmol) in CH$_2$Cl$_2$ (20 mL) was added SOCl$_2$ (0.60 mL) drop wise at 0° C. and was refluxed for 2 h. The volatiles were removed under reduced pressure to yield (S)-benzyl 2-(chlorocarbonyl)pyrrolidine-1-carboxylate] in CH$_2$Cl$_2$ and the reaction mixture was stirred at RT for 2 h. The volatiles were evaporated under reduced pressure. The residue was diluted with CH$_2$Cl$_2$ (100 mL), filtered and the filtrate was concentrated under vacuum. The crude residue was purified by column chromatography using 60% EtOAc/Hexane as eluent to afford compound 7 (750 mg, 45%).

$^1$H-NMR: (500 MHz, DMSO-d$_6$) (Rotamers): δ 7.36-7.23 (m, 8H), 7.15-7.12 (m, 3H), 5.21-5.15 (m, 2H), 5.04-4.92 (m, 1H), 4.57-4.50 (m, 2H), 3.88 (d, J=14.5 Hz, 1H), 3.65 (s, 3H), 3.54-3.46 (m, 3H), 3.21-3.13 (m, 1H), 3.02-2.90 (m, 2H), 2.19-2.02 (m, 4H), 1.97 (s, 3H), 1.89 (s, 1H), 1.77-1.65 (m, 1H), 1.17 (s, 2H), 1.06 (s, 2H).

Mass m/z: 594.1 [M$^+$+1].

Synthesis of (2S,3R)-methyl 3-acetoxy-2-(2-benzyl-1-((S)-pyrrolidine-2-carbonyl)-pyrrolidine-2-carboxamido) butanoate (8)

To a solution of compound 7 (200 mg, 0.336 mmol) in EtOAc (15 mL) was added 10% Pd/C (40 mg) was added under inert atmosphere and stirred for 12 h under H$_2$ atmosphere (balloon pressure). The reaction mixture was filtered through celite pad and concentrated under reduced pressure. The obtained residue was triturated with ether (10 mL) to afford compound 8 (125 mg, 81%) as solid.

$^1$H-NMR: (500 MHz, CDCl$_3$) (Rotamers): δ 7.88-7.87 (d, 1H, J=8.5), 7.30-7.26 (m, 2H), 7.24-7.21 (m, 1H), 7.13-7.12 (d, 2H, J=7), 5.44-5.43 (m, 1H), 4.76-4.74 (m, 1H), 3.94-3.92 (m, 1H), 3.84-3.81 (m, 1H), 3.75 (s, 3H), 3.50 (m, 1H), 3.26-3.12 (m, 3H), 2.90-2.88 (m, 1H), 2.23-2.15 (m, 4H), 2.04 (s, 3H), 1.87-1.77 (m, 5H), 1.27-1.24 (m, 3H).

Mass m/z: 460 (M+1).

Synthesis of Benzyl-2-(tert-butoxycarbonylamino)-3-hydroxybutanoate (10)

To a solution of 2-(tert-butoxycarbonylamino)-3-hydroxybutanoic acid (3.0 g, 13.69 mmol) in DMF (50 mL) was added $K_2CO_3$ (3.73 g, 27.39 mmol) and stirred at RT for 15 min. (Bromomethyl)benzene (2.81 g, 16.43 mmol) was added and stirred at RT for 6 h. The reaction mixture was diluted with water (50 mL) and extracted with EtOAc (2×50 mL). The combined organic layer was washed with brine (50 mL), dried over anhydrous $Na_2SO_4$ and concentrated under reduced pressure. The crude material was purified by silica gel column chromatography using 20% EtOAc/hexane as eluent to afford benzyl 2-(tert-butoxycarbonylamino)-3-hydroxybutanoate 10 (2.8 g, 66%).

$^1$H-NMR: (500 MHz, DMSO-$d_6$): δ 7.37-7.30 (m, 5H), 6.60 (d, J=8.5 Hz, 1H), 5.18-5.08 (m, 2H), 4.76 (d, J=7 Hz, 1H), 4.08-4.00 (m, 2H), 1.38 (s, 9H), 1.09 (d, J=6.0 Hz, 3H).

Mass m/z: 310.0 [M$^+$+1], 210 [M$^+$-De Boc].

Synthesis of benzyl-3-acetoxy-2-(tert-butoxycarbonylamino)-butanoate (11)

To a stirred solution of benzyl-2-(tert-butoxycarbonylamino)-3-hydroxybutanoate (2.8 g, 9.06 mmol) in THF (80 mL) was added $Ac_2O$ (1.1 g, 10.87 mmol), $Et_3N$ (1.51 mL, 10.87 mmol) and DMAP (280 mg) and stirred at RT for 15 min. The volatiles were removed under reduced pressure. The residue obtained was diluted with EtOAc (150 mL) and washed with cold 0.5N HCl solution (2×20 mL). The organic layer was washed with brine, dried over anhydrous $Na_2SO_4$ and concentrated under reduced pressure to afford 3-acetoxy-2-(tert-butoxycarbonylamino)-butanoate 11 (2.8 g, 88%).

$^1$H-NMR: (500 MHz, DMSO-$d_6$): δ 7.35-7.34 (m, 5H), 7.27-7.25 (d, J=8.5 Hz, 1H), 5.18-5.06 (m, 3H), 4.34-4.32 (m, 1H), 1.90 (s, 3H), 1.39 (s, 9H), 1.16 (d, J=3 Hz, 3H).

Mass m/z: 252 [M$^+$+1-De Boc].

Synthesis of (2S,3R)-3-acetoxy-2-(tert-butoxycarbonylamino)-butanoic acid (12)

Benzyl-3-acetoxy-2-(tert-butoxycarbonylamino) butanoate 11 (1.4 g, 3.98 mmol) was dissolved in EtOAc (40 mL), 10% Pd/C (600 mg) was added and reaction mixture was stirred under hydrogen atmosphere for 16 h. The reaction mixture was filtered over celite, solvent was evaporated in vacuo and the crude residue was triturated with hexane to yield (2S,3R)-3-acetoxy-2-(tert-butoxycarbonylamino) butanoic acid 12 (0.7 g, 70%).

$^1$H-NMR: (500 MHz, DMSO-$d_6$): δ 12.78 (br s, 1H), 6.94 (d, J=9.5 Hz, 1H), 5.16-5.14 (m, 1H), 4.17-4.15 (m, 1H), 1.95 (s, 3H), 1.39 (s, 9H), 1.10 (d, J=6.0 Hz, 3H).

Mass m/z: 260.0 [M-1].

Synthesis of (2S,3R)-methyl-3-acetoxy-2-(1-((S)-1-((2S,3R)-3-acetoxy-2-(tert-butoxycarbonyl-amino)-butanoyl)-pyrrolidine-2-carbonyl)-2-benzylpyrrolidine-2-carboxamido)-butanoate (13)

To a solution of compound (2S,3R)-3-acetoxy-2-(tert-butoxycarbonylamino)-butanoic acid 12 (199 mg, 0.76 mmol) in $CH_2Cl_2$ (6 mL) was under inert atmosphere were added IBCF (125 mg, 0.91 mmol) and NMM (154 mg, 1.52 mmol) at −15° C. and stirred for 1 h. A solution of (2S,3R)-methyl 3-acetoxy-2-(2-benzyl-1-((S)-pyrrolidine-2-carbonyl)pyrrolidine-2-carboxamido)-butanoate 8 (350 mg, 0.76 mmol) in DMF (2 mL) was added to the reaction mixture and stirred for 1 h at −15° C. The resultant reaction mixture was allowed to warm to RT and stirred for 19 h. The reaction mixture was extracted with EtOAc and the separated organic layer was washed with water (20 mL), followed by brine (20 mL), dried over $Na_2SO_4$ and concentrated under reduced pressure. The crude material was purified by preparative HPLC to afford compound 13 (100 mg, 20%).

$^1$H-NMR: (500 MHz, CD$_3$OD) (Rotamers): δ 7.30-7.24 (m, 3H), 7.15-7.13 (m, 2H), 4.62-4.55 (m, 2H), 4.29-3.97 (m, 1H), 3.98-3.79 (m, 4H), 3.75 (s, 3H), 3.62-3.22 (m, 2H), 3.23 (d, J=13.5 Hz, 1H), 3.00-2.95 (q, 1H), 2.37-2.31 (m, 1H), 2.23-2.10 (m, 2H), 2.02-1.88 (m, 3H), 1.46-1.28 (m, 2H), 0.97 (d, J=7.0 Hz, 6H).

Synthesis of N-((2S,3R)-1-amino-3-hydroxy-1-oxobutan-2-yl)-1-((S)-1-((2S,3R)-2-amino-3-hydroxybutanoyl)-pyrrolidine-2-carbonyl)-2-benzylpyrrolidine-2-carboxamide (D & E)

A solution of compound 13 (100 mg, 0.153 mmol) in methanolic-NH$_3$ (10 mL) was stirred in a sealed tube at RT for 72 h. The reaction mixture was concentrated under reduced pressure. The obtained crude residue was washed with ether (2×2 mL) to afford a diastereomeric mixture of Compound D & E (85 mg). 85 mg of this mixture was further purified by chiral preparative HPLC to yield 15 mg each of Compound D and E.

$^1$H-NMR: (500 MHz, CD$_3$OD) (Rotamers): δ 7.33-7.26 (m, 3H), 7.16 (s, 2H), 4.55-4.54 (m, 1H), 4.39 (s, 1H), 4.14 (s, 1H), 4.01-3.98 (m, 1H), 3.91-3.71 (m, 3H), 3.59 (s, 2H), 3.25-3.16 (m, 1H), 3.04-3.00 (m, 1H), 2.33-2.10 (m, 3H), 2.01-1.91 (m, 2H), 1.86-1.80 (m, 1H), 1.46-1.44 (m, 1H), 1.34-1.29 (m, 1H), 1.25-1.19 (m, 3H), 0.99-0.97 (d, J=14.0 Hz, 3H).

Mass m/z: 503 [M$^+$].

HPLC Purity: 98.1%.

Example 5

[$^3$H] MK-801 Binding Assay

This example demonstrates a [$^3$H] MK-801 binding assay that may be used to assess agonistic and/or antagonistic properties of candidate NMDA receptor modulators.

Crude synaptic membranes were prepared from rat forebrains as described in Moskal et al. (2001), "The use of antibody engineering to create novel drugs that target N-methyl-D-aspartate receptors," Curr. Drug Targets, 2:331-45. Male 2-3 month old rats were decapitated without anesthesia by guillotine, and the brains were rapidly removed (~90 sec) and whole cortex and hippocampus dissected on an ice cold platform, frozen on dry ice, and stored at −80° C. Samples were homogenized in 20 volumes of ice cold 5 mM Tris-HCl pH 7.4 by Brinkman Polytron and pelleted 48,000×g for 20 min at 4° C., and washed an additional 3 times as described above. Membranes were then resuspended in 5 mM EDTA and 15 mM Tris-HCl pH 7.4 and incubated for 1 hr at 37° C., membranes pelleted at 48,000×g for 20 min at 4° C., snap frozen in liquid nitrogen, and stored at −80° C. On the day of the experiment, membranes were thawed at room temperature and washed an additional 7 times in ice cold 5 mM Tris-HCl (pH 7.4) as described above. After the last wash, membranes were resuspended in assay buffer (5 mM Tris-acetate pH 7.4), and protein content was determined by the BCA assay.

[$^3$H] MK-801 binding assays were preformed as described in Urwyler et al. (2009), "Drug design, in vitro pharmacology, and structure-activity relationships of 3-acylamino-2-aminopropionic acid derivatives, a novel class of partial agonists at the glycine site on the N-methyl-D-aspartate (NMDA) receptor complex," J. Med. Chem., 52:5093-10. Membrane protein (200 μg) was incubated with varying concentrations of the test compounds ($10^{-3}$-$10^{-17}$ M) with 50 μM glutamate for 15 min at 23° C. Assay tubes were then incubated under non-equilibrium conditions with [$^3$H]MK-801 (5 nM; 22.5 Ci/mmol) for 15 min at 23° C. followed by filtration through Whatman GF/B filters using a Brandel M-24R Cell Harvester. Then the tubes were washed three times with assay buffer (5 mM Tris-acetate PH 7.4), and the filters were analyzed by liquid scintillation to calculate the disintegrations per minute (DPM). Zero levels were determined in the absence of any glycine ligand and in the presence of 30 μM 5,7-Dichlorokynurenic acid (5,7-DCKA). Maximal stimulation was measured in the presence of 1 mM glycine. 50 μM glutamate was present in all samples.

For each data point (i.e., a single concentration of the test compound), the % maximal [$^3$H] MK-801 binding was calculated by the following formula:

% maximal [$^3$H] MK-801 binding=
$((DPM_{test\ compound}-DPM_{5,7-DCKA})/(DPM_{1\ mM\ glycine}-DPM_{5,7-DCKA}))\times 100\%$ The efficacy for each compound, expressed as the % increase in [$^3$H] MK-801 binding, is calculated by fitting the data to a "log(agonist) vs. response (three parameters)" equation using Graph Pad Prism, with the efficacy for the test compound being the best-fit top value.

TABLE 1

[$^3$H] MK-801 Binding Assay Data.

| Compound | Potency | Efficacy (% Increase in [$^3$H] MK-801 Binding) |
|---|---|---|
| A | 5 pM | 79% |
| B | 6 pM | 24% |
| C | 16 pM | 23% |
| D | 0.2 pM | 12% |
| E | 0.2 pM | 12% |

Example 6

NMDA Receptor (NMDAR) Currents

This example demonstrates an assay for determining the effect of test compounds on NMDAR currents.

Experiments were conducted on hippocampal slices from 14-18 day old Sprague-Dawley rats as described in Zhang et al. (2008) "A NMDA receptor glycine site partial agonist, GLYX-13, simultaneously enhances LTP and reduces LTD at Schaffer collateral-CA1 synapses in hippocampus," Neuropharmacology, 55:1238-50. Whole cell recordings were obtained from CA1 pyramidal neurons voltage clamped at −60 mV, in slices perfused with (artificial cerebrospinal fluid) ACSF containing 0 mM [Mg2+] and 3 mM [Ca2+], plus 10 μM bicuculline and 20 μM CNQX to pharmacologically isolate NMDAR-dependent excitatory postsynaptic currents (EPSCs). Varying concentrations of test compound (10 nM to 1 μM) were bath applied and Schaffer collateral fibers were stimulated with single electrical pulses (80 μs duration) once every 30 s. NMDAR EPSCs were characterized by long rise and decay times, and were fully blocked at the end of each experiment by bath application of the NMDAR-specific antagonist D-2-amino-5-phosphonopentanoic acid (D-AP5; 50 μM). The efficacy of a test compound was calculated as the % increased in NMDAR current from the baseline. The baseline was measured as the NMDAR current before the test compound was applied.

TABLE 2

NMDAR Current Assay Data.

| Compound | Concentration | Efficacy (% Change in NMDAR Current from Baseline) |
|---|---|---|
| A | 1 μM | 70% |
| B | NT | NT |
| C | NT | NT |
| D | 1 μM | 75% |
| E | 1 μM | 10% |

NT = not tested.

Example 7

Long-Term Potentiation (LTP) Assay

This example demonstrates an assay for determining the effect of test compounds on LTP.

Hippocampal slices from 14-18 day old Sprague-Dawley rats were transferred to an interface recording chamber and continuously perfused at 3 ml/min with oxygenated ACSF at 32+0.5° C. Low resistance recording electrodes were made from thin-walled borosilicate glass (1-2 MΩ after filling with ACSF) and inserted into the apical dendritic region of the Schaffer collateral termination field in stratum radiatum of the CA1 region to record field excitatory postsynaptic potentials (fEPSPs). A bipolar stainless steel stimulating electrode (FHC Co.) was placed on Schaffer collateral-commissural fibers in CA3 stratum radiatum, and constant current stimulus intensity adjusted to evoke approximately half-maximal fEPSPs once each 30 s (50-100 pA; 100 ms duration). fEPSP slope was measured by linear interpolation from 20%-80% of maximum negative deflection, and slopes confirmed to be stable to within ±10% for at least 10 min before commencing an experiment. Long-term potentiation (LTP) was induced by a high frequency stimulus train (3×100 Hz/500 ms; arrow) at Schaffer collateral-CA1 synapses in control (vehicle), untreated slices, or slices pre-treated with test compound (10 nM to 100 μM). Long-term potentiation signals were recorded using a Multiclamp 700B amplifier and digitized with a Digidata 1322 (Axon Instruments, Foster City, Calif.). Data were analyzed using pClamp software (version 9, Axon Instruments) on an IBM-compatible personal computer. The efficacy was calculated as the % increase in long-term potentiation measured for slices pre-treated with test compound as compared to vehicle.

TABLE 3

LTP Assay Data.

| Compound | Concentration | Efficacy (% Increase from Vehicle) |
|---|---|---|
| A | NT | NT |
| B | NT | NT |
| C | NT | NT |
| D | 1 uM | 30% |
| E | 1 uM | 10% |

NT = not tested.

Example 8

Porsolt Test

This example demonstrates the Porsolt test for assessing test compounds for antidepressant activity.

Experiments were conducted as described in Burgdorf et al. (2009) "The effect of selective breeding for differential rates of 50-kHz ultrasonic vocalizations on emotional behavior in rats," Devel. Psychobiol., 51:34-46. Male Sprague-Dawley rats (2-3 month old) were dosed with test compound (0.3 to 30 mg/kg; intravenously via tail vein injection, or per os via gastric gavage) or vehicle (1 ml/kg sterile saline, or 1 ml/kg DMSO for 2,5-diazaspiro[3.4]octan-1-one) in a blind manner 1 hr before testing. Animals were placed in a 46 cm tall×20 cm in diameter clear glass tube filled to 30 cm with tap water at room temperature (23° C.±0.5° C.) for 5 min on the test day. All animals were towel dried after each swimming session by the experimenter. Water was changed after every other animal. Animals were videotaped and total duration (sec) of floating behavior (as defined as the minimal movement required in order to maintain the animal's head above the water) was quantified by a blind experimenter.

TABLE 4

Porsolt Assay Data.

| Compound | Dose, Route | % Reduction in Floating |
|---|---|---|
| A | 3 mg/kg, i.v. | 90% |
| B | NT | NT |
| C | NT | NT |
| D | 1 mg/kg, p.o. | 84% |
| E | 1 mg/kg, p.o. | 63% |

NT = not tested.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound represented by:

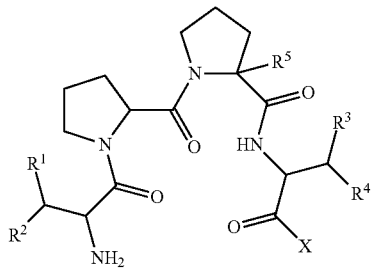

wherein:
$R^1$, $R^2$, $R^3$, and $R^4$ are each independently selected from the group consisting of hydrogen; halogen, $C_1$-$C_6$alkyl, and —OH;
$R^5$ is —$CH_2$-phenyl;
X is —$NH_2$; and
pharmaceutically acceptable salts, stereoisomers, and hydrates thereof.

2. The compound of claim 1 represented by:

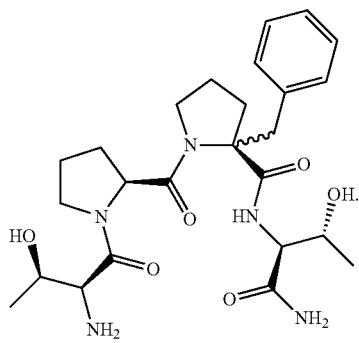

3. The compound of claim 1 represented by:

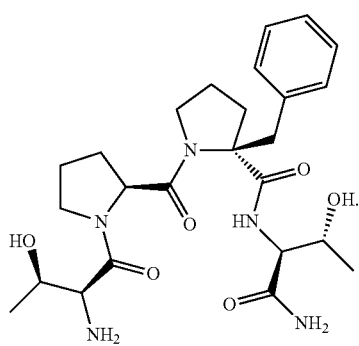 [SMILES: C[C@@H](O)[C@H](N)C(=O)N1CCC[C@H]1C(=O)N1CCCC1(Cc1ccccc1)C(=O)N[C@H](C(N)=O)[C@@H](C)O]

4. A pharmaceutical composition, comprising:
a therapeutically effective amount of a compound of claim 1 and a pharmaceutically acceptable carrier.

5. The pharmaceutical composition of claim 4, suitable for oral administration.

6. The pharmaceutical composition of claim 4, suitable for injection.

7. The compound of claim 1 represented by:

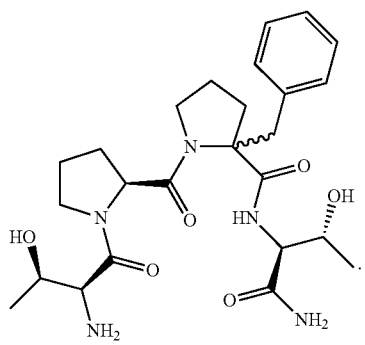

8. A compound represented by:

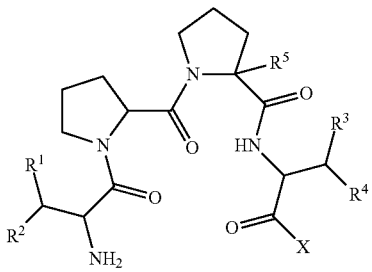

wherein:
  $R^1$, $R^2$, $R^3$, and $R^4$ are each independently selected from the group consisting of hydrogen; halogen, $C_1$-$C_6$alkyl, and —OH;
  $R^5$ is —$CH_2$-phenyl;
  X is selected from the group consisting of —OH, —O—$C_1$-$C_6$alkyl, —$NH_2$, —NH($C_1$-$C_6$alkyl), and —NH($C_1$-$C_6$alkyl)$_2$; and
pharmaceutically acceptable salts, stereoisomers, and hydrates thereof.

9. The compound of claim 8 represented by:

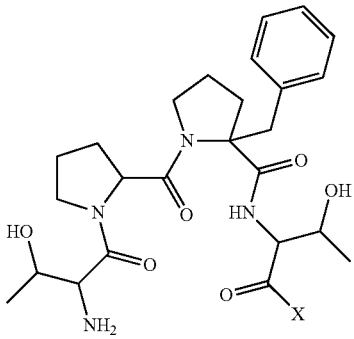

wherein X is OH or $NH_2$.

10. A compound represented by:

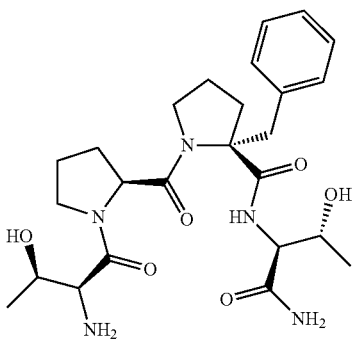 [SMILES: C[C@@H](O)[C@H](N)C(=O)N1CCC[C@H]1C(=O)N1CCC[C@@]1(Cc1ccccc1)C(=O)N[C@H](C(N)=O)[C@@H](C)O]

and pharmaceutically acceptable salts and hydrates thereof.

11. A pharmaceutical composition, comprising:
  a therapeutically effective amount of a compound of claim 10 and a pharmaceutically acceptable carrier, wherein the pharmaceutical composition is suitable for oral administration.

12. A pharmaceutical composition, comprising:
  a therapeutically effective amount of a compound of claim 10 and a pharmaceutically acceptable carrier, wherein the pharmaceutical composition is suitable for injection.

* * * * *

UNITED STATES PATENT AND TRADEMARK OFFICE
CERTIFICATE OF CORRECTION

PATENT NO. : 8,673,843 B2
APPLICATION NO. : 13/525861
DATED : March 18, 2014
INVENTOR(S) : Joseph Moskal et al.

It is certified that error appears in the above-identified patent and that said Letters Patent is hereby corrected as shown below:

In the Claims:

At column 42, claim 2 line number 10, please delete the chemical structure and insert the chemical structure -- 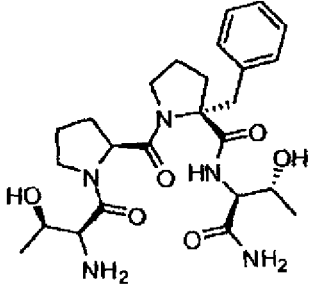 -- in its place.

Signed and Sealed this
First Day of July, 2014

Michelle K. Lee
*Deputy Director of the United States Patent and Trademark Office*